(12) United States Patent
Petronis et al.

(10) Patent No.: US 8,043,808 B2
(45) Date of Patent: Oct. 25, 2011

(54) CPG-AMPLICON AND ARRAY PROTOCOL

(75) Inventors: Arturas Petronis, Toronto (CA); Axel Schumacher, Munich (DE)

(73) Assignee: Centre for Addiction and Mental Health, Toronto, Ontario ( * ) Notice: Subject to any disclaimer, the term of this patent is extended or adjusted under 35 U.S.C. 154(b) by 554 days.

(21) Appl. No.: 10/598,140

(22) PCT Filed: Feb. 18, 2005

(86) PCT No.: PCT/CA2005/000211
§ 371 (c)(1),
(2), (4) Date: Feb. 9, 2007

(87) PCT Pub. No.: WO2005/078121
PCT Pub. Date: Aug. 25, 2005

(65) Prior Publication Data
US 2008/0064030 A1 Mar. 13, 2008

Related U.S. Application Data

(60) Provisional application No. 60/545,732, filed on Feb. 18, 2004.

(51) Int. Cl.
C12Q 1/68 (2006.01)
(52) U.S. Cl. ........................................................ 435/6.1
(58) Field of Classification Search ........................ None
See application file for complete search history.

(56) References Cited

U.S. PATENT DOCUMENTS

| 5,874,215 A * | 2/1999 | Kuiper et al. ..................... 435/6 |
| 6,110,680 A * | 8/2000 | Sutcliffe et al. ................... 435/6 |
| 6,605,432 B1 * | 8/2003 | Huang ............................... 435/6 |
| 6,617,137 B2 * | 9/2003 | Dean et al. ..................... 435/91.1 |
| 2003/0099997 A1 | 5/2003 | Bestor | |

FOREIGN PATENT DOCUMENTS

| WO | 97/45560 A | 12/1997 |
| WO | WO 00/26401 | 5/2000 |
| WO | WO 03/027259 | 4/2003 |
| WO | WO 03/064701 | 8/2003 |

OTHER PUBLICATIONS

Yan et al. (J Nutr. Aug. 2002;132(8 Suppl):2430S-2434S).*
Chotai et al. (J Med Genet. Jun. 1998;35(6):472-5).*
Yan et al. (2002) "Applications of CpG Island Microarrays for High-Throughput Analysis of DNA Methylation" J. Nutrition 132(8) Suppl.:2430S-2434S.
Chotai & Payne (1998) "A rapid, PCR based test for differential molecular diagnosis of Prader-Willi and Angelman syndromes" J. Med. Genet. 35(6):472-475.
International Search Report and Written Opinion for PCT/CA2005/000211.
Adorjan, P., et al., Tumour class prediction and discovery by microarray-based DNA methylation analysis. Nucleic Acids Res, 2002. 30(5): p. e21.
Balog, R.P., et al., Parallel assessment of CpG methylation by two-color hybridization with oligonucleotide arrays. Anal Biochem, 2002. 309(2): p. 301-10.
Bird, A.P., CpG-rich islands and the function of DNA methylation. Nature, 1986. 321(6067): p. 209-13.
Chen C. et al. Methylation target array for rapid analysis of CpG island hypermethylation in multiple tissue genomes. Am J Pathol. Jul. 2003. vol. 163, No. 1, pp. 37-45.
Frommer, M., et al., A genomic sequencing protocol that yields a positive display of 5-methylcytosine residues in individual DNA strands. PNAS USA, 1992. 89(5): p. 1827-31.
Gitan, R.S., et al., Methylation-specific oligonucleotide microarray: a new potential for high-throughput methylation analysis. Genome Res, 2002. 12(1): p. 158-64.
Hatada, I., et al., A microarray-based method for detecting methylated loci. J Hum Genet, 2002.47(8): p. 448-51.
Hou, P., et al., A microarray to analyze methylation patterns of p16(Ink4a) gene 5'-CpG islands. Clin Biochem , 2003 . 36(3): p. 197-202.
Kruger et al. McrB: a prokaryotic protein specifically recognizing DNA containing modified cytosine residues. EMBO J, 1995. 14(11): p. 2661-9.
Shi, H., et al., Triple analysis of the cancer epigenome: an integrated microarray system for assessing gene expression, DNA methylation, and histone acetylation. Cancer Res, 2003. 63(9): p. 2164-71.
Stewart & Raleigh, Dependence of McrBC cleavage on distance between recognition elements . Biol Chem, 1998. 379(4-5): p. 611-6.
Sutherland et al., McrBC: a multisubunit GTP-dependent restriction endonuclease. J Mol Biol , 1992. 225(2): p. 327-48.
Tompa, R., et al ., Genome-wide profiling of DNA methylation reveals transposon targets of CHROMOMETHYLASE3. Curr Biol, 2002. 12(I): p. 65-8.
Toyota, M., et al ., Identification of differentially methylated sequences in colorectal cancer by methylated CpG island amplification. Cancer Res, 1999. 59(10): p. 2307-12.
Van Steensel et al., Chromatin profiling using targeted DNA adenine methyltransferase. Nat Genet, 2001. 27(3): p. 304-8.
Van Steensel & Henikoff, Epigenomic profiling using microarrays. Biotechniques , 2003. 35(2): p. 346-50, 352-4, 356-7.
Yamada, Y. et al. A comprehensive analysis of allelic Methylation status of CpG islands on human chromosome 21q. Genome Res. Feb. 2004, vol. 14, No. 2, pp. 247-266.
Yan, P.S., et al., Dissecting complex epigenetic alterations in breast cancer using CpG island microarrays. Cancer Res, 2001. 61(23): p. 8375-80.
Yan, P.S., et al., Use of CpG island microarrays to identify colorectal tumors with a high degree of concurrent methylation. Methods, 2002. 27(2): p. 162-9.
Frigola, Jordi et al., Methylome Profiling of Cancer Cells by Amplification of Inter-Methylated Sites (AIMS), Oxford University Press, Nucleic Acids Research, 2002, vol. 30, No. 7 e28, 2002, pp. 1-7.
Supplemental European Search Report for EP 05 70 6493 dated Dec. 3, 2007.

* cited by examiner

Primary Examiner — Christopher M. Babic
(74) Attorney, Agent, or Firm — Suzannah K. Sundby; Smith, Gambrell & Russell, LLP

(57) ABSTRACT

The invention can be summarized as follows. There is provided a method for amplifying hypomethylated genomic nucleotide sequences and/or hypermethylated genomic nucleotide sequences and comparing the methylation state between different samples, for example control and test samples. Also disclosed is a microarray based method for analyzing hypo and/or hypermethylated genomic nucleotide sequence. Further, kits comprising reagents for practicing the method are provided.

9 Claims, 11 Drawing Sheets

CPG-AMPLICON AND ARRAY PROTOCOL

This application is a 371 national phase entry of PCT/CA2005/000211 filed Feb. 18, 2005 and claims the benefit of priority to U.S. Patent Application Ser. No. 60/545,732, filed 18 Feb. 2004, which is herein incorporated by reference in its entirety.

FIELD OF INVENTION

The present invention relates to methods and systems for epigenetic profiling. More specifically, the present invention relates to methods and systems for assessing methylation levels of nucleotide sequences.

BACKGROUND OF THE INVENTION

Many lines of evidence have shown that modification of cytosine bases residing in the dinucleotide sequence CpG in vertebrate genomes plays an essential role in regulating a variety of genome functions such as X chromosome inactivation, parental imprinting, inactivation of genomic retroelements, and differential gene expression. Across the human genome, about 80% of the CpG dinucleotides are heavily methylated, but some areas remain unmethylated, preferentially in the GC rich CpG islands [Bird, A. P., *CpG-rich islands and the function of DNA methylation*. Nature, 1986. 321(6067): p. 209-13.]. DNA methylation can perform its regulatory function through the differential marking of genes. Cytosine methylation is a stable but potentially reversible process that allows for the temporal and spatial-specific regulation of gene in higher organisms.

Several different strategies have been applied to detect methylated CpG dinucleotides in eukaryotic genomes (reviewed in [van Steensel, B. and S. Henikoff, *Epigenomic profiling using microarrays*. Biotechniques, 2003. 35(2): p. 346-50, 352-4, 356-7]). The most frequently used method is the bisulfite modification-based strategy, developed by Frommer et al. [Frommer, M., et al., *A genomic sequencing protocol that yields a positive display of 5-methylcytosine residues in individual DNA strands*. Proc Natl Acad Sci USA, 1992. 89(5): p. 1827-31.]. In this method, bisulfite converts unmethylated cytosine bases to uracil, whereas methylated cytosines remain unaltered. Such sequences can be directly sequenced using the Sanger sequencing method or can be interrogated using microarrays. In such microarrays, oligonucleotide pairs that differ by having either a cytosine or a thymine at a methylatable position of a cytosine can discriminate the two nucleotides by incubating at a temperature that allows only exact matches between the probe and the oligonucleotide Adorjan, P., et al., *Tumour class prediction and discovery by microarray-based DNA methylation analysis*. Nucleic Acids Res, 2002. 30(5): p. e21; Gitan, R. S., et al., *Methylation-specific oligonucleotide microarray: a new potential for high-throughput methylation analysis*. Genome Res, 2002. 12(1): p. 158-64; Balog, R. P., et al., *Parallel assessment of CpG methylation by two-color hybridization with oligonucleotide arrays*. Anal Biochem, 2002. 309(2): p. 301-10; Hou, P., et al., *A microarray to analyze methylation patterns of p16(Ink4a) gene 5'-CpG islands*. Clin Biochem, 2003. 36(3): p. 197-202.

Several other methods of providing methylation status on a global scale including microarray experiments have been published. In a method called differential methylation hybridization (DMH) [Huang, T. H., U.S. Pat. No. 6,605,432 B1 issued Aug. 12, 2003.], genomic DNA (gDNA) from breast cancer cells were treated with the four-base cutter MseI that restricts gDNA into small fragments of 100-200 bp. This enzyme rarely cuts in CpG-rich regions, leaving many CpG islands intact. MseI cleavage is followed by ligation of end adaptors specific for MseI sticky-ends, cleavage with the methylation-sensitive enzyme BstUI, and subsequent PCR amplification. This method results in amplification of its hypermethylated fraction of gDNA, and ignores the hypomethylated or unmethylated fraction.

Microarrays in this study contains DNA fragments representing various CpG islands. Several other publications used the step of enrichment for the hypermethylated fraction of a given genome [Yan, P. S., et al., *Applications of CpG island microarrays for high-throughput analysis of DNA methylation*. J Nutr, 2002. 132(8 Suppl): p. 2430S-2434S;. Yan, P. S., et al., *Use of CpG island microarrays to identify colorectal tumors with a high degree of concurrent methylation*. Methods, 2002. 27(2): p. 162-9; Shi, H., et al., *Triple analysis of the cancer epigenome: an integrated microarray system for assessing gene expression, DNA methylation, and histone acetylation*. Cancer Res, 2003. 63(9): p. 2164-71; Toyota, M., et al., *Identification of differentially methylated sequences in colorectal cancer by methylated CpG island amplification*. Cancer Res, 1999. 59(10): p. 2307-12; Yan, P. S., et al., *Dissecting complex epigenetic alterations in breast cancer using CpG island microarrays*. Cancer Res, 2001. 61(23): p. 8375-80]. Amplification of non-methylated sequences is suppressed by the digestion of the template DNA before PCR with the restriction enzymes BstUI and HpaII, which are blocked by methylation of their target sequence [Yan, P. S., et al., *Dissecting complex epigenetic alterations in breast cancer using CpG island microarrays*. Cancer Res, 2001. 61(23): p. 8375-80]. The resulting hypermethylated DNA fraction was used to compare the methylation patterns from tumor and control tissues by hybridizing to microarrays containing randomly cloned genomic fragments that were enriched in CpG islands A related method uses a digestion step with SmaI, followed by digestion with XmaI, which is a methyl-insensitive isoschizomer of SmaU [Hatada, I., et al., *A Microarray-based method for detecting methylated loci*. J Hum Genet, 2002. 47(8): p. 448-51.]. The cleavage with SmaI produces blunt end DNA fragment, whereas the cleavage products of XmaI contains protruding ends, which are ligated to specific XmaI-adaptors. After a PCR that uses primers specific for these adaptors, the resulting amplification products, which consist mainly of methylated 5'-CCCGGG-3' sequences, are hybridized to microarrays.

Another method that uses methylation-sensitive restriction enzymes for fractionating DNA was presented by Tompa et al. [Tompa, R., et al., *Genome-wide profiling of DNA methylation reveals transposon targets of CHROMOMETHYLASE3*. Curr Biol, 2002. 12(1): p. 65-8.]. This strategy used the methylation sensitive enzyme MspI, which cleaves 5'CCGG-3' but is blocked by methylation of the outer cytosine ($^m$5'-CCGG-3'). Digested DNA samples were size-fractionated on sucrose gradients (5%-30%) by ultracentrifugation as previously described [van Steensel, B., J. Delrow, and S. Henikoff, *Chromatin profiling using targeted DNA adenine methyltransferase*. Nat Genet, 2001. 27(3): p. 304-8.]. Gradient fraction containing plant DNA fragments smaller than 2.5 kb, as determined by gel-electrophoresis, were pooled and concentrated by isopropanol precipitation. Tester and control samples were then labeled with Cy3- or Cy5-dCTP by random priming and co-hybridized to microarrays that contained spotted PCR amplification products that primarily represented randomly chosen locations from the *Arabidopsis* genome [Tompa, R., et al., *Genome-wide profil-*

*ing of DNA methylation reveals transposon targets of CHROMOMETHYLASE3.* Curr Biol, 2002. 12(1): p. 65-8].

Wang (WO 03/027259, published Apr. 3, 2003) discloses cleavage of mouse genomic DNA with the methyl-sensitive enzyme HpaII, ligation of adaptors specific for HpaII sticky-ends, and PCR using Cy-3 or Cy-5 labeled primers. The amplicons produced by this method may retain methylated sequences that are in between the cleaved HpaII restriction sites.

Martienssen et al. (US 2004/0132048, published Jul. 8, 2004) suggest methods to obtain methylated or unmethylated fractions of genomic DNA obtained by cleavage with methyl-dependent enzymes such as McrBC that specifically cleave methylated sequences, or by cleavage with, for example, HpaII which does not cleave methylated sequences. Similar to Wang, the Martienssen et al. methods may be complicated by retention of methylated sequences between unmethylated restriction sites. Furthermore, there may be retention of unmethylated sequences between the methylated restriction sites. Another drawback of these methods is a step of physically separating the cleaved methylated or unmethylated fractions from the rest of the genomic DNA by gel electrophoresis, size exclusion chromatography and size differential centrifugation in a sucrose gradient. Methods using a physical separation step require relatively large amounts of starting material due to inefficiencies of DNA recovery inherent in the separation step.

There is a need in the art to develop new methods and systems for epigenetic profiling. Further there is a need in the art for new methods and systems for epigenetic profiling of chromosomes and genomes. Further still, there is a need in the art to develop methods and systems to assess methylation levels of probed loci such as repetitive elements, genes, imprinting elements, promoters, enhancer elements, intron sequences and whole genomes.

SUMMARY OF THE INVENTION

The present invention relates to methods and systems for epigenetic profiling. More specifically, the present invention relates to methods and systems for assessing methylation levels of nucleotide sequences.

According to the present invention there is provided a method of analysing the methylation state of one or more nucleotide sequences comprising the steps of:
a) selecting one or more genomic test nucleotide sequences from one or more subjects that exhibit a phenotype of interest, and one or more corresponding genomic control sequences from one or more control subjects that lack the phenotype of interest;
b) digesting the genomic test nucleotide sequences and separately digesting the genomic control sequences with one or more methylation sensitive restriction endonucleases, to produce ends that can be ligated to an adaptor nucleotide sequence;
c) ligating adaptor nucleotide sequences to the ends produced from step b) to produce ligated sequences;
d) cleaving the ligated sequences with one or more CpG methylation specific endonucleases, to produce amplifiable test nucleotide sequences, non-amplifiable test nucleotide sequences, amplifiable control nucleotides sequences and non-amplifiable control nucleotide sequences;
e) amplifying the amplifiable test nucleotide sequences and amplifiable control nucleotide sequences to produce amplified test nucleotide sequences and amplified control nucleotide sequences;
f) labelling the amplified test nucleotide sequences from step e) with a first label, and labelling the amplified control nucleotide sequence from step e) with a second label;
g) hybridising the labelled products of step f) with an array comprising a series of nucleotide sequences that are capable of hybridising thereto;
h) determining the ratio of the signals emitted by the first label relative to the second label for each hybridised nucleotide sequence on the array.

The present invention further contemplates a method of analysing the methylation state of one or more nucleotide sequences comprising the steps of:
a) selecting one or more genomic test nucleotide sequences from one or more subjects that exhibit a phenotype of interest and one or more corresponding genomic control sequences from one or more control subjects that lack the phenotype of interest;
b) digesting the genomic test nucleotide sequences and separately digesting the genomic control sequences with one or more frequent cutting restriction endonucleases;
c) ligating adaptor nucleotide sequences to the ends produced from step b to produce ligated sequences;
d) cleaving the ligated sequences with one or more methylation sensitive restriction endonucleases to produce amplifiable test nucleotide sequences, non-amplifiable test nucleotide sequences, amplifiable control nucleotides sequences and non-amplifiable control nucleotide sequences;
e) amplifying the amplifiable test nucleotide sequences and amplifiable control nucleotide sequences to produce amplified test nucleotide sequences and amplified control nucleotide sequences;
f) labelling the amplified test nucleotide sequences from step e) with a first label, and labelling the amplified control nucleotide sequence from step e) with a second label;
g) hybridising the labelled products of step f) with an array comprising a series of nucleotide sequences that are capable of hybridising thereto;
h) determining the ratio of the signals emitted by the first label relative to the second label for each set of hybridised nucleotide sequences on the array.

The present invention also contemplates a method for identifying or detecting effects of DNA sequence variation in a methylation-state-analysis of one or more nucleotide sequences comprising the steps of:
a) selecting one or more genomic test nucleotide sequence from one or more subjects that exhibit a phenotype of interest, for example a disease such as but not limited to cancer, diabetes, Alzheimer's disease, schizophrenia or the like, and one or more corresponding genomic control sequences from one or more control subjects that lack the phenotype of interest;
b) amplifying the genomic test nucleotide sequences and separately amplifying the genomic control sequences with a DNA polymerase, for example without limitation a Phi29 DNA polymerase, to produce an unmethylated copy of the genomic test nucleotide sequences and an unmethylated copy of the genomic control sequences;
c) treating the unmethylated copy of the genomic test nucleotide sequences and separately treating the unmethylated copy of the genomic control sequences with restriction endonuclease digestion, adaptor ligation, amplification, labelling, array hybridisation, and ratio determination steps that are equivalent to corresponding steps in the methylation-state-analysis;
d) comparing the one or more ratios determined in step c) to the one or more ratios of the methylation-state-analysis, thereby identifying or detecting effects of DNA sequence variation in the methylation-state-analysis.

The present invention also contemplates a method as defined above wherein the phenotype of interest comprises a disease, for example, but not limited to cancer, diabetes, Alzheimer's disease, schizophrenia, multiple sclerosis, psoriasis, atherosclerosis, asthma, autism, rheumatoid arthritis or other disease. However, the present invention also contemplates employing the method of the present invention to analyze the methylation state or changes in the methylation state of one or more genomic nucleotide sequences in subjects, for example, but not limited to human subjects, or in cell cultures that are treated with a drug or the like, or that are subject to one or more specific physical stimuli or conditions.

The present invention further contemplates a method as defined above wherein the frequent cutting restriction endonuclease is selective for A/T rich sequences over C/G sequences, for example Csp61, Tas1, or a combination thereof.

The present invention further contemplates a method as defined above wherein the probe is a chemically reactive fluorophore, for example, but not limited the first probe may be Cy3 and the second probe may be Cy5.

The present invention further contemplates a method as defined above wherein the methylation restriction endonucleases comprise a cocktail comprising HpaII, Bsu15I (ClaI), Hin6I, AciI (SsiI) and TaiI.

Also contemplated by the present invention as defined above is the use of a CpG methylation-specific restriction endonuclease such as, without limitation, McrBC, McrA, or MrrA.

The present invention further contemplates a kit comprising one or more genomic test nucleotide sequences, one or more corresponding genomic control nucleotide sequences, one or more frequent cutting restriction endonucleases, one or more specific adaptor nucleotide sequences, one or more methylation-sensitive restriction endonucleases, one or more CpG methylation-specific restriction endonucleases, one or more probes for labelling the nucleotide sequences, one or more microarrays capable hybridising to the genomic test and control nucleotide sequences, software for displaying and/or analysing the sequences hybridised to the microarray, reagents and/or enzymes for amplifying nucleotide sequences, or any combination thereof.

The methods of the present invention allow for enrichment of an unmethylated fraction or a methylated fraction due to adaptor-ligation and adaptor-specific amplification. Accordingly, the present invention does not require a step of physically separating a cleaved methylated or unmethylated fraction from the rest of the genomic DNA by, for example, gel electrophoresis, size exclusion chromatography and size differential centrifugation in a sucrose gradient.

Thus far, 'epigenomic' microarray approaches have been based on the enrichment of the hypermethylated DNA and predominantly used for identification of abnormally methylated CpG islands in malignant cells. Although this strategy seems to be useful for detection of major epigenetic changes in some regions of the genome, the overall proportion of the interrogated CpG sites is substantially lower in comparison to the approach based on the analysis of the unmethylated fraction. The inventors have discovered that interrogation of the unmethylated fraction of genomic DNA may be up to several hundred-fold more efficient in comparison to the hypermethylated fraction scenario.

The present invention provides methods that can overcome a complication of methylated sequences being retained between unmethylated restriction sites, and unmethylated sequences being retained between the methylated restriction sites. For example, in order to delete internally methylated ligation fragments, ligation products may be treated with one or more methyl-specific enzymes, such as, without limitations, McrBC or MrrA. As another example, in order to delete internally unmethylated ligation-fragments, ligation products may be treated with methylation-sensitive restriction enzymes such as, without limitation, HpaII, Hin6I, AciI or HpyCH4IV. Ligation products were incubated for 8 h at 37° C. in a mixture containing 10 U/microgram HpaII, 6 U/microgram Hin6I and 8 U/microgram AciI in 2×Y+/Tango buffer (Fermentas).

Another advantage of the methylation profiling methods of the present invention is the possibility to work with limited DNA resources. Although the standard protocol requires from 0.5 microgram-1 microgram of genomic DNA, the amount of the template DNA can be significantly lower. It seems feasible to apply the enrichment protocol also for single cells, which would allow a quantitative measurement of methylation.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 1 shows a diagrammatic depiction of an example of the present invention

FIG. 2A: The gel pictures show that Lambda DNA fragments between ~250 bp and ~1.5 kb were consistently amplified, while the human DNA fragments were not amplified. To assess the accuracy of the enrichment methods, Lambda DNA was cut with methylation-sensitive restriction enzymes (HpyCH4IV, HpaII or Hin6I) and mixed with an excess of human genomic DNA, which was cleaved with a methylation-insensitive restriction enzyme (EcoRI). The mixed DNA fragments were ligated to the adaptor U-CG1, and then amplified in an adaptor-specific PCR. Amplification products were compared with a cleaved product of native Lambda DNA on a 1% agarose gel. FIG. 2B: shows a DNA smear between ~0.2 kb and ~2.5 kb in a standard adaptor-PCR (with 68° C. annealing) indicating an efficient ligation and amplification. The size of the amplification products varies with the annealing temperature used for PCR. Usually, a high annealing/elongation temperature will lead to an increased product size. FIG. 2C: Scatter-plot that shows a comparison of ligation products treated with McrBC vs. the untreated sample on the COMT array. McrBC treated fragments that contained methylated CpG dinucleotides were cleaved and could not be amplified in the following adaptor-PCR, resulting in reduced signal intensities in the Cy5 channel.

FIG. 3A: Structure and GC-content of the chromosomal region on human chromosome 22q11.2 that spans the catechol-o-methyltransferase gene (COMT), the thioredoxin reductase 2 gene (TXNRD2), and the annadillo repeat gene deleted in VCFS (ARVCF). FIG. 3B: To determine the methylation profile of the 100 kb COMT region, 50-mer oligonucleotides (black horizontal bars) were designed based on the restriction sites for the methylation-sensitive endonucleases, HpaII, Hin6I and AciI (additional alternative enzymes are HpyCH4IV or Hin1I). Depending on the methylation status of the CpG4-nucleotides several combinations of amplicons (grey horizontal bars) can potentially hybridize to the oligonucleotides. FIG. 3C: Typical hybridization patterns on the oligonucleotide-microarray showing that the complexity and informativeness of the hybridization signals increases with increasing number of methylation-sensitive restriction enzymes.

FIG. 4A: Scatter plot diagram representing two sets of amplification products derived from the same DNA source but produced at different timepoints by different researchers. The high correlation coefficient of spot-intensities demonstrates a high reproducibility of the method. FIG. 4B: Influence of the PCR cycle number. Scatter plot diagrams show hybridization signal intensities of the unmethylated fraction that was amplified using 20 PCR cycles (Cy3 channel) and 30 cycles (Cy5 channel). Amplification products of each PCR were co-hybridized to the COMT microarray that contained oligonucleotides representing single copy sequences (black circles), partially repetitive sequences (grey squares; >20 copies/genome) and highly repetitive DNA fragments (white squares; >100 copies/genome), such as ALU and LINE repeats. The 2-step annealing-extension PCR produced an unbiased amplification. FIG. 4C: Scatter plot representing the unmethylated fraction of human genomic DNA 'spiked' with different amounts of control DNA. The test samples contained either a 16-fold excess of Lambda DNA (16 genome equivalents [GE] vs. 1 GE) or a 16-fold excess of pBR322 (128 GE vs. 8 GE), respectively. The amplicons of the spiked DNA (representing unmethylated DNA) can be easily distinguished as outliers, whereas the signals representing genomic DNA are located close to the regression line. Median signal intensities of different length oligonucleotides (40-50 bp) that target a specific HpaII restriction fragment in Lambda DNA reveal that the length of spotted sequences directly influences the spot intensity and therefore the sensitivity of the microarray. FIG. 4D: Sensitivity of the CpG-island microarray hybridization. 2 mg of control GDNA was labeled with Cy5 and co-hybridized with 2 microgram (0% difference), 1.9 microgram (5% difference), 1.8 microgram (10% difference), 1.5 microgram (25% difference) or 1.0 microgram (50% difference) of Cy3-labeled gDNA. For each hybridization, the regression lines represent the overall intensity that mimics methylation differences over the entire sample. The decrease of amount of DNA is reflected in the angle of the regression lines, which deviated by 5%-7% from the expected values.

FIG. 5A: Changes of methylation profiles at TXNRD2-COMT-ARVCF in a brain tumor. The data from two different microarrays experiments are superimposed over each other. The analysis of two post-mortem brain samples (black dots) reveals no major difference in methylation levels, whereas the signal intensities vary significantly in the brain tumor (white dots) when compared to the normal brain. FIG. 5B: Comparison of unmethylated TXNRD2-COMT-ARVCF fractions in the Jurkat and mucosal cells. The scatter plot suggests significant overall gene region-wide methylation differences in the COMT, TXNRD2, and ARVCF genes between the two cell-types. FIG. 5C: Co-hybridization of enriched unmethylated and hypermethylated fragments derived from the same DNA source. A large portion of amplicons is present only in one of the enriched fractions. Whereas the unmethylated fraction contains only amplicons that harbour CpG dinucleotides, the hypermethylated fraction also contains fragments that do not contain methylatable cytosines. FIG. 5D: Comparison of DNA methylation profiles in the brain tissues of a healthy control and a schizophrenia patient.

FIG. 7 shows representative scatter plots obtained using the methods of the present invention.

DETAILED DESCRIPTION

The following description is of a preferred embodiment.

Figure 1A:
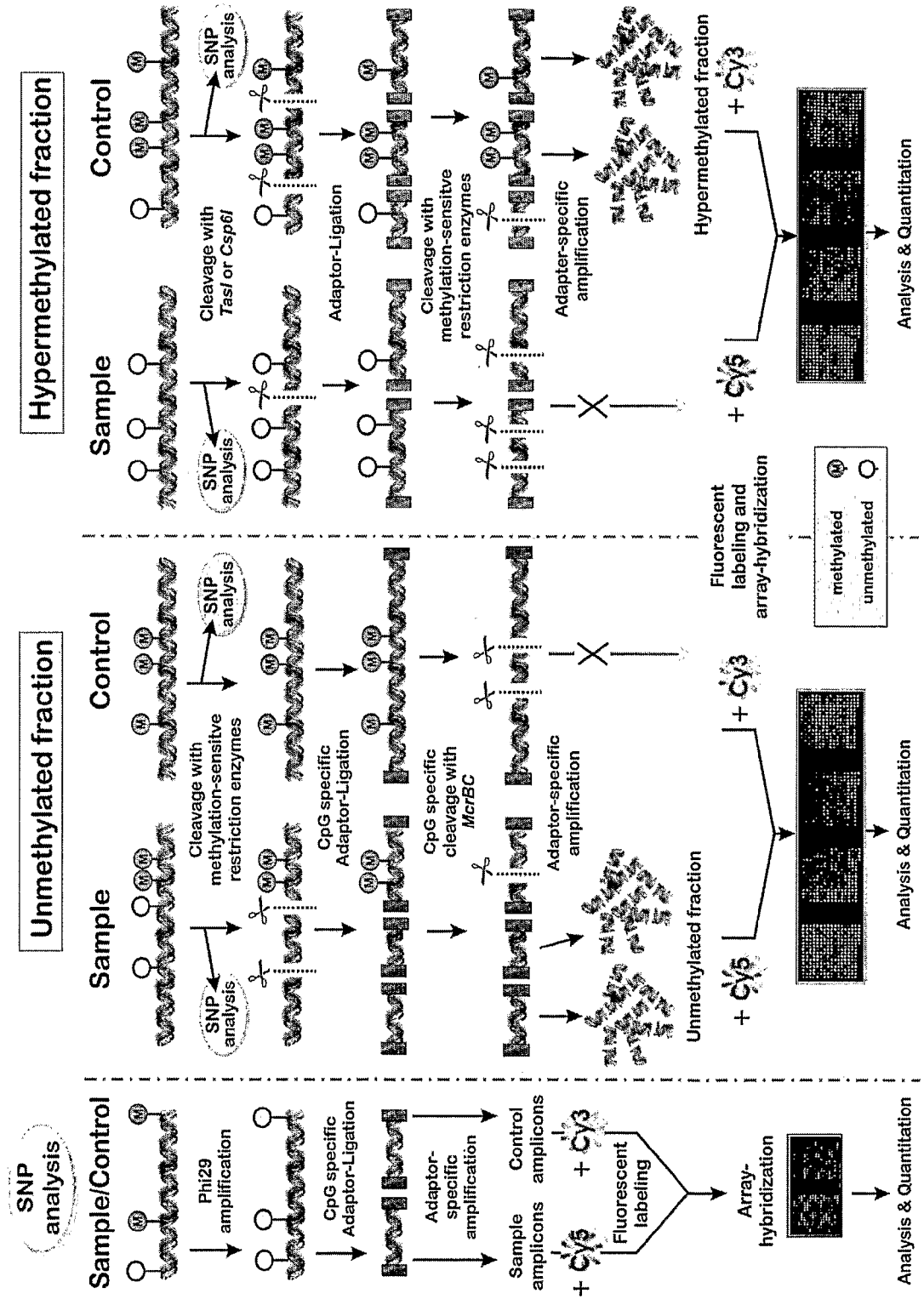
FIG. 1A is a schematic outline of the microarray-based method for identification of DNA methylation differences and DNA polymorphisms in genomic DNA. Left panel: Analysis of DNA sequence variation. Middle panel: Isolation and enrichment of unmethylated DNA fragments. Control and tester DNA are cleaved by methylation-sensitive restriction endonucleases, and the resulting DNA fragments are then selectively enriched by adaptor-specific aminoallyl-PCR's, labeled, and hybridized to microarrays. Right panel: Alternative procedure to enrich the hypermethylated. DNA fraction.

According to an embodiment of the present invention and referring generally to FIG. 1, there is provided a method of analysing the methylation state of one or more nucleotide sequences. The method of the present invention may comprise the steps as shown on the middle panel of FIG. 1, the right panel of FIG. 1, or both the middle and right panels of FIG. 1. In a further aspect of the invention, the steps shown in the left panel of FIG. 1 may be used for correcting the effect of DNA sequence variation on the differential methylation analysis. In addition, the method of the present invention may comprise any combination of steps shown in FIG. 1, for example on the right panel, the left panel or a combination thereof.

An example of the present invention, which is not meant to be limiting in any manner, provides a method of analysing the methylation state of one or more nucleotide sequences comprising the steps of:
a) selecting one or more genomic test nucleotide sequences from one or more subjects that exhibit a phenotype of interest, for example a disease such as but not limited to cancer, diabetes, Alzheimer's disease, schizophrenia, or any other disease that may be effected by differential DNA methylation or aberrant DNA methylation, and one or more corresponding genomic control sequences from one or more control subjects that lack the phenotype of interest;
b) digesting the genomic test nucleotide sequences and separately digesting the genomic control sequences with one or more methylation sensitive restriction endonucleases, for example a cocktail comprising HpaII, Bsu15 (ClaI), Hin6I, AciI (SsiI) and TaiI to produce ends that can be ligated to an adaptor nucleotide sequence;
c) ligating adaptor nucleotide sequences to the ends produced from step b) to produce ligated sequences;
d) cleaving the ligated sequences with one or more CpG methylation-specific endonucleases, for example, but not limited to McrBC to produce amplifiable test nucleotide sequences, non-amplifiable test nucleotide sequences, amplifiable control nucleotides sequences and non-amplifiable control nucleotide sequences;
e) amplifying the amplifiable test nucleotide sequences and amplifiable control nucleotide sequences to produce amplified test nucleotide sequences and amplified control nucleotide sequences;
f) labelling the amplified test nucleotide sequences from step e) and optionally labelling the non-amplified test nucleotide sequence from step d) with a first label, for example, but not limited to a chemically reactive fluorophore, for example, but not limited to the fluorophore being Cy 3, and labelling the amplified control nucleotide sequence from step e) and optionally labelling the non-amplified control nucleotide sequence from step d) with a second label, for example, a chemically reactive fluorophore, for example, but not limited to the fluorophore being Cy 5;
g) hybridising the labelled products of step f) with an array comprising a series of nucleotide sequences that are capable of hybridising thereto;
h) determining the ratio of the signals emitted by the first label and the second label for each hybridised nucleotide sequences on the array.

An example of the method as described above is shown diagrammatically by the middle panel of FIG. 1.

Most array-based epigenetic studies target the hypermethylated DNA sequences. Although analysis of hypermethylated fractions is a valid approach, interrogation of the unmethylated fraction may be much more informative. For example, in the 100 kb region comprising the catechol-o-methyltransferase gene (COMT) of chr 22, which contains 2,193 methylatable cytosines enrichment of the unmethylated fraction would theoretically generate ~401 amplicons of sufficient size ($\geqq$50 bp), each representing the methylation status of at least one cytosine. In contrast, the combination of MseI (+BsuI, to remove unmethylated fragments), the most frequently used enzymes for enrichment of the hypermethylated fraction would produce 227 amplicons. Seventy-seven amplicons would either contain no CpG dinucleotides or they would be too short to hybridize stringently to a microarray. Of the remaining 150 fragments, 144 contain multiple CpGs; hence, they are not fully informative since a single unmethylated restriction site would eliminate the entire fragment from the eventual amplification. Overall, most of the truly informative CpG dinucleotides are not targeted using the BsuI approach and none of these CpG dinucleotides are targeted by BsuI. In experiments with the microarray types (see Example 1), PCR products from the unmethylated fraction produced strong signals (signal to noise ratio >6) for up to 98% of all arrayed clones/oligos, whereas the hypermethylated fraction produced fewer signals (up to 86%). On average, the unmethylated fraction detected approximately 18% more spots. Computer-based analysis of 50 randomly picked CpG island sequences revealed that, for example, the unmethylated fraction derived from HpaII cleavage results in approximately 22 times more fragments (19.9 fragments/kb) of a preferred size range (75-2,000 bp) than the hypermethylated fraction (0.9 fragments/kb) using MseI.

Nevertheless, analysis of the hypermethylated DNA fraction may also add relevant information to the methylation profiles. Accordingly, in another example of the present invention, there is provides a method of analysing the methylation state of one or more nucleotide sequences comprising the steps of:
a) selecting one or more genomic test nucleotide sequences from one or more subjects that exhibit a phenotype of interest, for example a disease such as but not limited to cancer, diabetes, Alzheimer's disease, schizophrenia or the like, and one or more corresponding genomic control sequences from one or more control subjects that lack the phenotype of interest;
b) digesting the genomic test nucleotide sequences and separately digesting the genomic control sequences with one or more frequent cutting restriction endonucleases, preferably selective for A/T rich sequences, for example, but not limited to Csp6I and Tas1 to produce ends that can be ligated to an adaptor nucleotide sequence;
c) ligating adaptor nucleotide sequences to the ends produced from step b to produce ligated sequences;
d) cleaving the ligated sequences with one or more methylation sensitive restriction endonucleases to produce amplifiable test nucleotide sequences, non-amplifiable test nucleotide sequences, amplifiable control nucleotides sequences and non-amplifiable control nucleotide sequences;

e) amplifying the amplifiable test nucleotide sequences and amplifiable control nucleotide sequences to produce amplified test nucleotide sequences and amplified control nucleotide sequences;
f) labelling the amplified test nucleotide sequences from step e) and optionally labelling the non-amplified test nucleotide sequence from step d) with a first label, for example, but not limited to a chemically reactive fluorophore, for example, but not limited to the fluorophore being Cy 3, and labelling the amplified control nucleotide sequence from step e) and optionally labelling the non-amplified control nucleotide sequence from step d) with a second label, for example, a chemically reactive fluorophore, for example, but not limited to the fluorophore being Cy 5;
g) hybridising the labelled products of step f) with an array comprising a series of nucleotide sequences that are capable of hybridising thereto;
h) determining the ratio of the signals emitted by the first label and the second label for each hybridised nucleotide sequences on the array.

An example of the method as described above may be found as depicted on the right panel of FIG. 1.

Alternatively, the step of digesting (step b) in above method mat be substituted with the following step:
b) digesting the genomic test nucleotide sequences and separately digesting the genomic control sequences with one or more methyl sensitive enzyme, followed by digestion of the genomic test nucleotide sequences and the genomic control sequences with a methyl-insensitive enzyme that produces a different end, either a blunt or a sticky end. The methyl insensitive enzyme may be a neoschizomer of the corresponding methyl sensitive enzyme. For example, BsiSI is a methyl insensitive enzyme (for $C/(^{met}C)GG$) and produces an end ($^{met}C$)GG which is different than end produced by Sth302II, a methyl sensitive enzyme (for CC/GG) to produce the blunt end GG. Another example includes, XmaI is a methyl insensitive enzyme (for $C/C(^{met}C)GGG$) and produce an end $C(^{met}C)GGG$ which is different than an end produced by SmaI or PaeBI, methyl sensitive enzymes (for CCC/GGG) to produce the blunt end GGG.

Still another example of the present invention provides a method of identifying or correcting for effects of DNA sequence variation in a methylation-state-analysis of one or more nucleotide sequences comprising the steps of:
a) selecting one or more genomic test nucleotide sequence from one or more subjects that exhibit a phenotype of interest, for example a disease such as but not limited to cancer, diabetes, Alzheimer's disease, schizophrenia or the like, and one or more corresponding genomic control sequences from one or more control subjects that lack the phenotype of interest;
b) amplifying the genomic test nucleotide sequences and separately amplifying the genomic control sequences with a DNA polymerase, for example without limitation a Phi29 DNA polymerase, to produce an unmethylated copy of the genomic test nucleotide sequences and an unmethylated copy of the genomic control sequences;
c) treating the unmethylated copy of the genomic test nucleotide sequences and separately treating the unmethylated copy of the genomic control sequences with restriction endonuclease digestion, adaptor ligation, amplification, labelling, array hybridisation, and ratio determination steps that are equivalent to corresponding steps in the methylation-state-analysis;
d) comparing the one or more ratios determined in step c) to the one or more ratios of the methylation-state-analysis, thereby identifying DNA sequence variation in a methylation-state-analysis.

Figure 8:
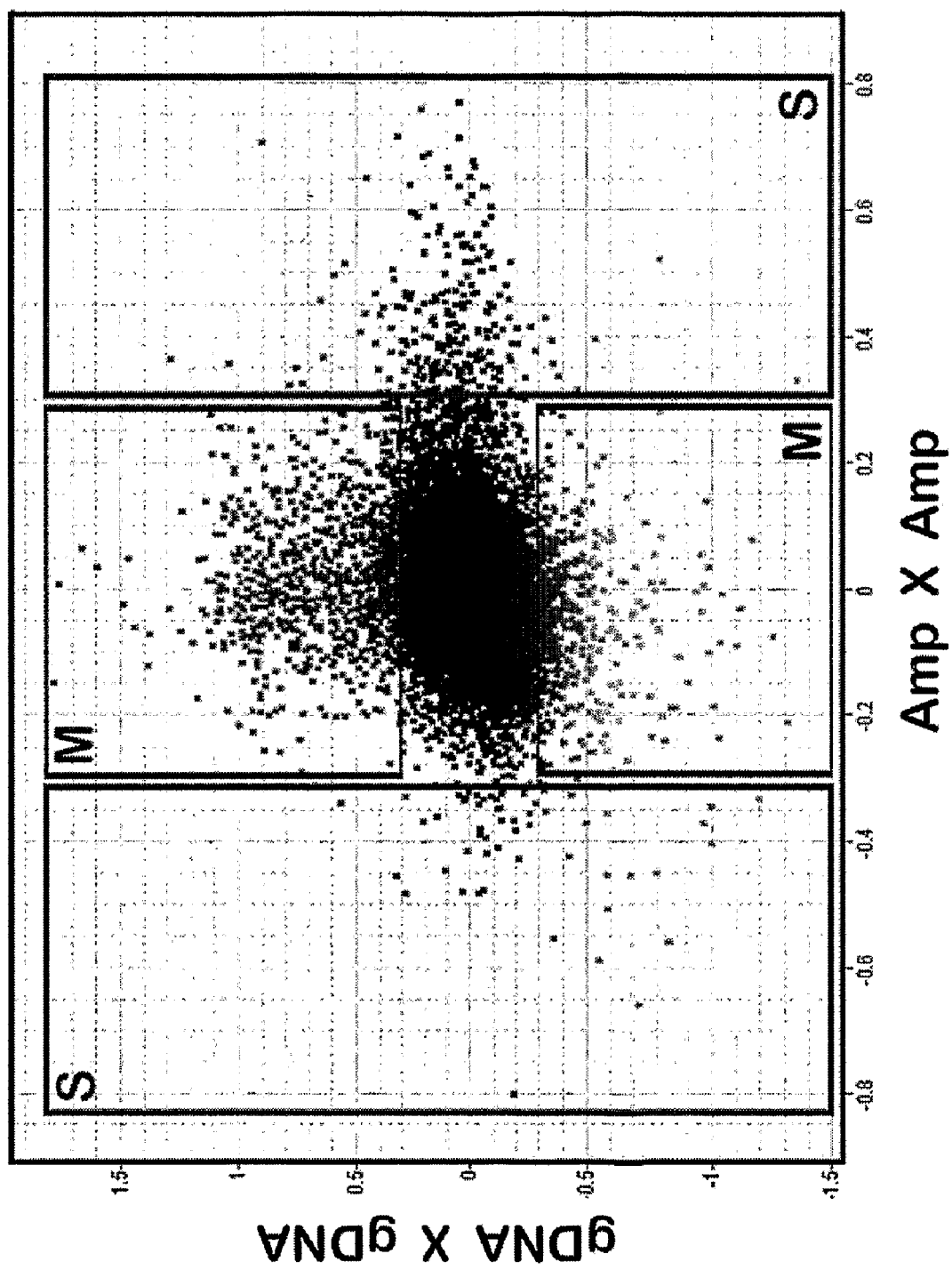
FIG. 8 shows an example of the present invention that provides for combined methylation- and SNP-analysis on a CpG island microarray. The data of two separate hybridizations of DNA samples derived from two individuals are plotted against each other. The y-axis contains the data derived from a methylation analysis (triple-cleavage with HpaII, Hin6I, and AciI), whereas the x-axis contains the SNP-data derived from the hybridization of the same DNA samples, which were subjected to the entire genome amplification prior to cleavage by the methylation-sensitive restriction enzymes. Significant outliers (log-ratio <−0.3, >0.3) can be classified into four clusters (S=SNPs, M=DNA methylation differences), enabling the differentiation of epigenetic differences and nucleotide polymorphisms between the test-samples. Amp=Whole-genome amplified sample; gDNA=genomic DNA.

The left panel of FIG. 1 shows an example of a correction method to be used in conjunction with a methylation-state-analysis based on enrichment of an unmethylated fraction as described, for example, in the middle panel of FIG. 1. However, the correction method shown in the left panel may easily be adapted to be used with the methylation-state-analysis that enriches for methylated fractions of genomic DNA as shown, for example, in the right panel of FIG. 1 by simply using equivalent cleavage, adaptor-ligation, and adapter-specific amplification steps as those used in the methylation state-analysis that enriches for methylated fractions of genomic DNA. FIG. 8 shows a representative scatter plot demonstrating the advantages of using the corrective analysis of DNA sequence variation in conjunction with a methylation-state-analysis. The correction method described above may be performed before, or after the method of analysing the methylation state of one or more nucleic acid sequences as described above.

The present invention also contemplates a combination of the methods disclosed above, for example, but not limited to as shown generally by FIG. 1.

The method of the present invention may be employed to identify specific nucleotide sequences that may be hypermethylated or hypomethylated in diseases relative to control genomic sequences and thus provide specific targets for therapeutic intervention. Further, the method may provide diagnostic and/or prognostic indicators for a disease.

The method of the present invention may also be employed with cell cultures, for example, but not limited to monitor and measure methylation changes after cells are treated with a biological agent, for example, but not limited to a drug, or after they are subjected to specific environmental conditions or stimuli.

The methylation sensitive restriction enzymes do not interrogate every cytosine. Accordingly, the methods of the present invention may be used in conjunction with other techniques in order to gain more information regarding epigenetic DNA modifications. For example, array-based analysis can readily include both the DNA methylation analysis of the present invention and histone modification analysis through the chromatin immunoprecipitation (ChIP) technology, which identifies DNA sequences associated with modified histones. DNA and histone modifications seem to be dependent, and consequently the possibility of a combinatorial approach that interrogates both DNA methylation and chromatin modification in parallel might be a productive approach in fine mapping of epigenetic changes. The method of the present invention also maybe used in combination with other methods to detect and quantify methylated DNA, for example, but not limited to the bisulfate method as described previously, or any other method as is known in the art.

The present invention further contemplates a kit comprising one or more genomic test nucleotide sequences, one or more corresponding genomic control nucleotide sequences, one or more frequent cutting restriction endonucleases, one or more specific adaptors nucleotide sequences, one or more methylation-sensitive restriction endonucleases, one or more CpG specific restriction endonucleases, one or more probes for labelling the nucleotide sequences, one or more microarrays capable hybridising to the genomic test and control nucleotide sequences, software for displaying and/or analysing the sequences hybridised to the microarray, reagents and/or enzymes for amplifying nucleotide sequences, or any combination thereof. It will be understood that the reagents and/or enzymes for amplifying nucleotide sequences may pertain to the amplification step in methylation-state-analysis, the amplification step in DNA sequence variation analysis, or the amplification in both of these analyses.

In an embodiment of the present invention, the method as described above provides for an array-based DNA methylation analysis of genomic nucleotide sequences, for example, but not limited to genes, repetitive elements such as but not limited to ALUs, LINEs etc . . . , enhancer elements, repressor elements, chromosomal regions, whole chromosomes/genomes or any combination thereof Representative steps of the method that are not meant to be limiting in any manner are shown in FIG. 1.

Referring now to FIG. 1, there is shown a diagrammatic depiction of an embodiment of the present invention. The procedure is described for a "sample" and "control", however as will be evident to a person of skill in the art, the term "sample" may comprise a genomic test nucleotide sequence from a subject that exhibits a particular phenotype and the "control" may comprise a genomic control sequence from a control subject wherein the phenotype is absent. For example, but not wishing to be limiting in any manner, the sample may be from a subject that exhibits a disease phenotype, for example, but not limited to cancer (for example but not limited to cancer of the breast, brain, bone, blood, prostate, skin cancer, etc) diabetes, Alzheimer's, hypertension, multiple sclerosis, psoriasis, atherosclerosis, asthma, autism, rheumatoid arthritis or any other disease that may be effected by differential DNA methylation or aberrant DNA methylation. Conversely, the "control" does not exhibit the phenotype.

To enrich for the hypermethylated fraction of genomic DNA (see right panel of FIG. 1), the DNA is cleaved first with a frequent cutting restriction endonuclease, preferably a restriction endonuclease specific for A/T rich sequences, which produces ends in the DNA that can be ligated to an adaptor nucleotide sequence. Several enzymes with a 4-bp recognition sequence are known which produce sticky ends. For example, but not wishing to be limiting in any manner, Csp6I and TasI produce suitable ends. After the ligation of a TasI or Csp6I specific adaptor nucleotide sequences comprising internal sequences suitable for PCR amplification, the samples are cleaved with one or more methylation-sensitive restriction enzymes for example, but not limited to HpaII, AciI (SsiI), Bsu15I (ClaI) anchor Hin6I (HhaI), preferably a cocktail comprising 2, 3, 4, 5 or more of such enzymes. Consequently, substantially all unmethylated fragments are cut and cannot be amplified in the following PCR reaction. The PCR products of the sample and control are separately labeled with fluorescent dyes, combined, and hybridized to an oligo-array for example, but not limited to a COMT-ARVCF array, cDNA array or a CpG island microarray. The quantitation and analysis of array data permits a detailed comparison of the methylation status between sample and control.

To enrich the hypomethylated/unmethylated fraction of DNA in the sample and control (see middle panel of FIG. 1), the DNA is cleaved with one or more, preferably a cocktail of methylation-sensitive restriction enzymes, for example, but not limited to HpaII, Bsu15I (ClaI), Hin6I, AciI (SsiI), TaiI or any combination thereof. Depending on the methylation status of the samples, these enzymes produce more or less fragments with sticky ends on which one or several adaptor nucleotide sequences can be ligated. Subsequently, the ligation products are subjected to an amplification procedure, which uses the adaptor sequences as primers. Therefore, as shown in FIG. 1, depending on the enzymes chosen, it is possible to enrich hypo- or hypermethylated fragments of nucleotide sequences in a sample and control. The resulting DNA fragments may be labeled in the PCR reaction (indirect labeling method) or labeled after the PCR reaction (direct labeling method). Finally, the labeled products are hybridized to arrays, which contain short oligo sequences, and the fluorescent markers are quantified and analyzed.

DNA sequence variations, for example, DNA polymorphisms, at a restriction site relevant to the methods of the present invention may simulate DNA modification differences across individuals. Data from the SNP consortium indicate that roughly every 360th nucleotide in the human genome represents a SNP. In humans approximately 2.16 million SNPs are detectable in CpG dinucleotides, and such CpG SNPs are 6.7-fold more abundant than expected. See the NCBI Single Nucleotide Polymorphism website at ncbiDOTnlmDOTnihDOTgov/SNP, wherein "DOT" is ".". Depending on the restriction enzyme combination, CpG island array-based studies shown in FIG. 8 indicate that 10%/30% of all outliers that were originally detected as methylation differences contained SNPs. Information on the SNPs within the restriction sites of the enzymes used for the enrichment of the unmethylated or hypermethylated fractions is helpful in differentiating the epigenetic variations from the DNA sequence variations.

In order to correct for DNA sequence variation effects on the methylation-state-analysis with respect to either the hypermethylated or hypomethylated/unmethylated fraction an equivalent array experiment is performed using a copy of genomic sample and control DNA that is stripped of all methylated cytosines. For example, FIG. 1 (left panel) shows the use of Phi29 DNA polymerase to amplify whole genomic DNA, which creates a copy of the genome with all methylated cytosines replaced by unmethylated cytosines. The unmethylated copy of the sample and control genomic DNA is then treated with equivalent restriction cleavage, adaptor-ligation, adaptor-specific amplification, labeling, array hybridization, analysis and quantitation steps as used in the DNA methylation-state-analysis. This data can then be plotted against the corresponding DNA methylation data. With regards to performing a corrective DNA sequence variation analysis with a methylation-state-analysis that enriches for the unmethylated fraction it will be understood that cleavage with the methylation-specific enzyme may optionally be omitted in the DNA sequence variation analysis as this analysis is performed with a copy of genomic DNA that is devoid of methylation and therefore would not be expected to be cleaved by a methylation-specific restriction enzyme.

During the restriction cleavage of template DNAs, the reaction is preferably spiked with array-specific oligonucleotides that function as normalization controls for example, but not limited to Lambda, Arabidopsis, prokaryotic plasmid sequences or a combination thereof.

In the embodiment shown in the middle panel of FIG. 1, adaptor nucleotide sequences specific for the unmethylated CpG-dinucleotides are ligated to the hypomethylated DNA fragments whereas the hypermethylated (uncut) DNA regions remain unmodified. Long fragments, which could still contain methylated CpGs are cut by a CpG specific restriction endonuclease, for example, but not limited to McrBC. Without wishing to be considered limiting in any manner or bound by theory, McrBC is thought to cut only if two or more mCPGs are present in a DNA fragment. In a subsequent PCR reaction, primers complementary to the CpG-adaptors are used to preferentially amplify the hypomethylated DNA fragments in the sample and control.

Figure 1B:
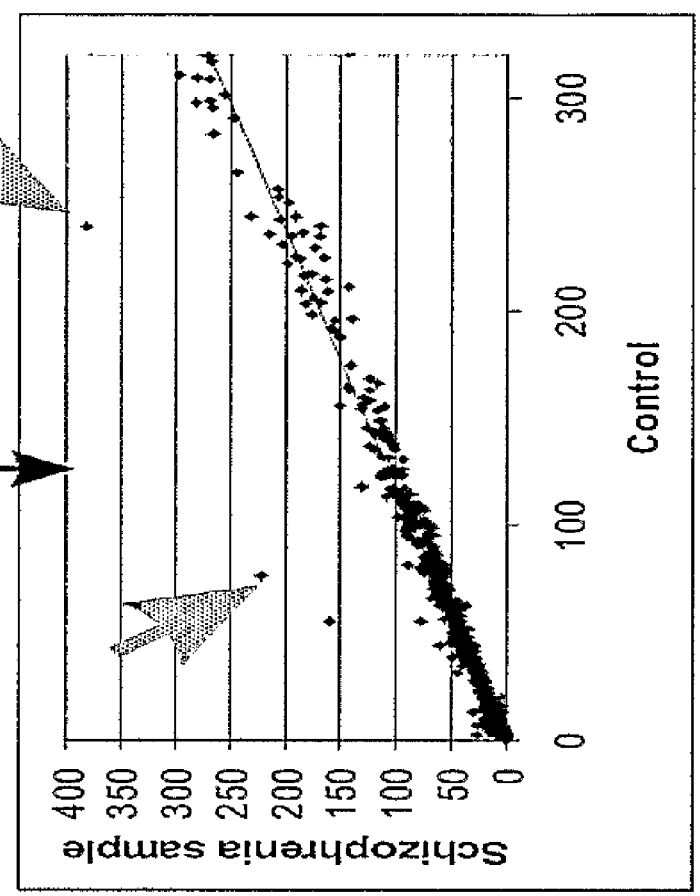
FIG. 1B shows an example of a scatter plot that reveals differences in DNA methylation patters between samples and controls. Two large arrows indicate hybridization signals that deviate from the regression line.

FIG. 1B shows an example of a scatter plot derived from a "catechol-o-methyltransferase, armadillo repeat gene deleted in VCFS syndrome" (COMT-ARVCF) array, which reveals differences in DNA methylation patterns between samples and controls (see in particular the arrows in FIG. 1).

In an embodiment of the present invention, the method employs specific adaptor nucleotide sequences that are highly specific for the protruding ends, generated by the aforementioned restriction enzymes. The adaptor nucleotide sequences preferably contain a small sequence-specific protruding end and a non-target homologous core sequence. The adaptor nucleotide sequences may also comprise a specific antisense-overhang that prevents tandem repeat formation and blunt-end ligation, a "disruptor" sequence, which disrupts the restriction sites after ligation, a non-5'-complementary end and a new restriction site that facilitates the cleavage of the adaptor from the target sequences if desired, or a combination thereof.

The following adaptor nucleotide sequences are exemplary and are not meant to limit the invention in any manner. The term "adaptor" and "adaptor nucleotide sequence" are used interchangeably.

Adaptor Nucleotide Sequences (a) The CpG-overhang specific universal adaptor "U-CG1" for the hypomethylated DNA fraction is an adaptor that fits to DNA ends produced by the following methylation-sensitive restriction enzymes: HpaII, MspI, Hin6I, Bsu15I (ClaI), AciI (SsiI), Psp1406I (AclI), Bsp119I (AsuII), Hin1I (AcyI), XmiI (AccI) and the methylation-insensitive enzyme Taq1. The adaptor is the annealing product of the two primers:

```
U-CG1a:
5'-CGTGGAGACTGACTACCAGAT-3',       SEQ ID NO: 1

U-CG1b:
5'-AGTTACATCTGGTAGTCAGTCTCCA-3',   SEQ ID NO: 2
```

(b) The ACGT-overhang specific adaptor "ACGT-1" for the hypomethylated DNA fraction is an adaptor that fits to DNA ends produced by the methylation-sensitive restriction enzyme TaiI. The adaptor is the annealing product of these two primers:

```
ACGT-1a:
5'-GAGACTGACTACCAGAT-3',           SEQ ID NO: 3

ACGT-1b:
5'-AGTTACATCTGGTAGTCAGTCTCACGT-3', SEQ ID NO: 4.
```

(c) The AATT-overhang specific adaptor "AATT-1" for the hypermethylated DNA fraction is an adaptor that fits to DNA ends produced by the methylation-insensitive restriction enzyme TasI (TspEI). The adaptor is the annealing product of these two primers:

```
AATT-1a:
5'-GAGACTGACTACCAGAT-3',           SEQ ID NO: 5

AATT-1b:
5'-AGTTACATCTGGTAGTCAGTCTCAATT-3', SEQ ID NO: 6
```

(d) The TA-overhang specific adaptor "TA-1" for the hypermethylated DNA fraction is an adaptor that fits to DNA ends produced by the methylation-insensitive restriction enzyme Csp6I. The adaptor is the annealing product of these two primers:

```
TA-1a:
5'-TATGAGACTGACTACCAGAT-3',        SEQ ID NO: 7

TA-1b:
5'-AGTTACATCTGGTAGTCAGTCTCA-3',    SEQ ID NO: 8
```

The adaptors are ligated by a T4 ligase to the restriction fragments produced by the enzymes specific for the hyper- and hypomethylated DNA fractions.

To enrich hyper- and hypomethylated fractions, both ligation-pools are subjected to specific restriction cleavage prior to PCR amplification: The hypomethylated ligation-fragments are cleaved by CpG specific restriction endonuclease, for example, but not limited to, McrBC. McrBC from *Escherichia coli* K-12 is a restriction enzyme that belongs to the family of AAA+ proteins and cleaves DNA containing methylcytosine on one or both strands [Sutherland, E., L. Coe, and E. A. Raleigh, *McrBC: a multisubunit GTP-dependent restriction endonuclease.* J Mol Biol, 1992. 225(2): p. 327-48; Kruger, T., C. Wild, and M. Noyer-Weidner, McrB: *a prokaryotic protein specifically recognizing DNA containing modified cytosine residues.* Embo J, 1995. 14(11): p. 2661-9; Stewart, F. J. and E. A. Raleigh, *Dependence of McrBC cleavage on distance between recognition elements.* Biol Chem, 1998. 379(4-5): p. 611-6.]. McrBC does not substantially cut unmethylated DNA. Sites on the DNA recognized by McrBC may consist of two half-sites of the form $(G/A)^{m}C$. Without wishing to be limiting in any manner or bound by theory, these half-sites may be separated by up to about 3 kb, but are preferably separated by about 55 to about 103 base pairs. McrBC acts upon a pair of $Pu^{m}CG$ sequence elements, thereby detecting a high proportion of methylated CpGs within the ligation-fragments, but does not appreciably recognize HpaII/MspI sites (CCGG) in which the internal cytosine is methylated.

Figure 2:
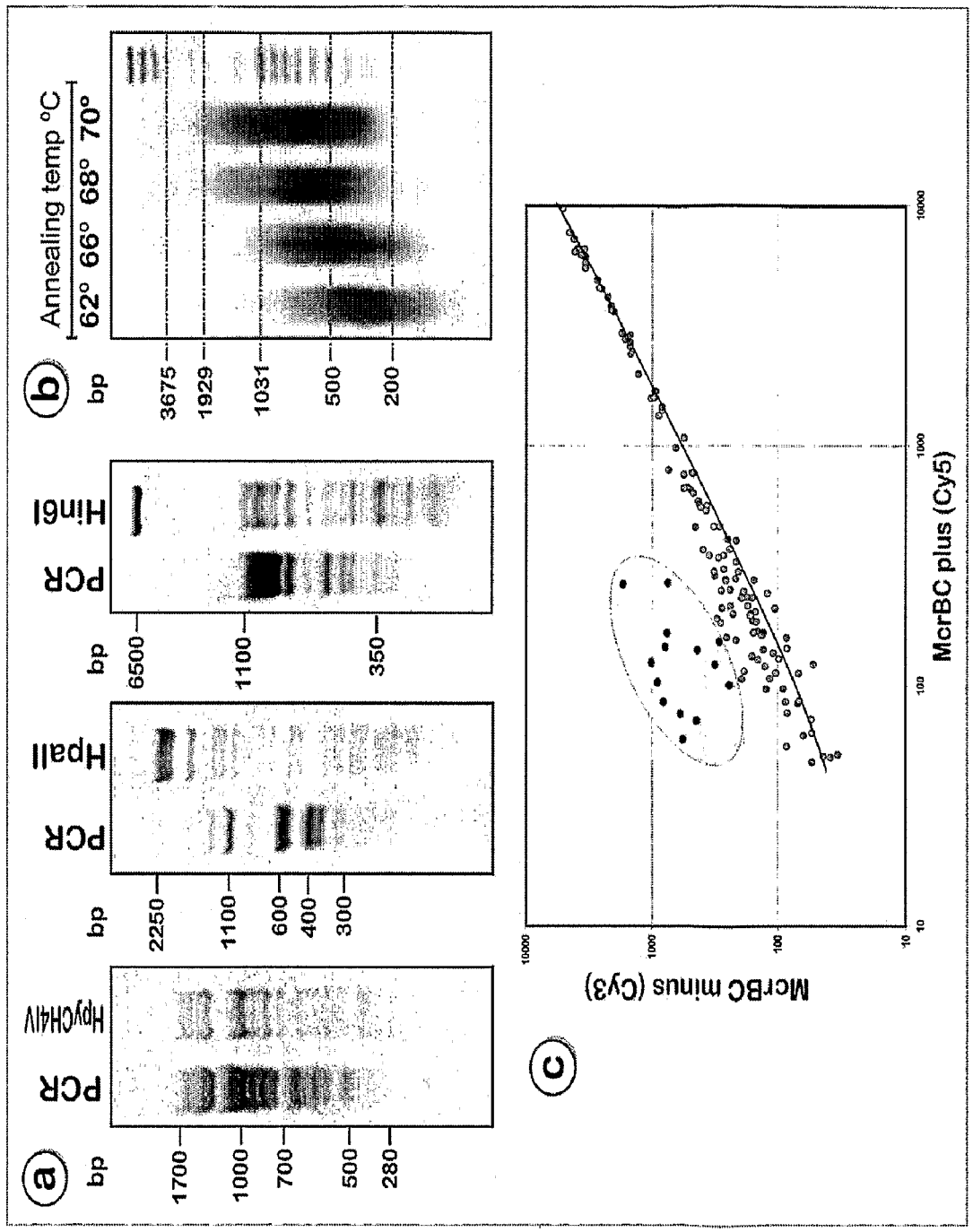
FIG. 2 shows an example of the present invention that achieves a selective enrichment of restriction fragments with the universal adaptor U-CG1.

Referring now to FIG. 2c there is shown a graphic depiction of a scatter plot of a comparison of a McrBC treated ligation versus an untreated ligation on the COMT-ARVCF array. As shown in FIG. 2c, McrBC treated fragments are cut and cannot be amplified in the adaptor-PCR, therefore the signal will be much lower on the array (shown in the Cy5 channel).

The hypermethylated ligation-fragments are preferably cleaved by specific combinations of the restriction enzymes HpaII, MspI, Hin6I, Bsu15I (ClaI), AciI (SsiI), Psp1406I (AclI), Bsp119I (AsuII), Hin1I (AcyI) or XmiI (AccI) depending on the stringency of the approach. In an embodiment of the present invention, which is not meant to be limiting in any manner, all of the enzymes are employed. In an alternate embodiment any of about 4 to about 9 enzymes may be employed. Also, it is contemplated that other enzymes not listed below may be employed in combination with one or more enzymes listed above.

After restriction cleavage of the DNA-fractions, ligation products are amplified with primers specific for the adaptors used in the assay. Either the amplicon-fragments are labeled already during the PCR for example, but not limited to by allyl-labeling (the standard method uses aminoallyl (aa) nucleotide incorporation followed by coupling to N-hydroxysuccinim de (NHS) functionalized dyes (for example, but not limited to FluoroLink monofunctional dyes from Amersham/(UK)) or a standard PCR with normal dNTPs is performed with subsequent labeling of the amplification products by random priming. In another example labeled primers may be used to perform the PCR reaction.

For the amplification of small amounts of DNA (for example, but not limited to from micro-dissected tissues, the amplicons are amplified by a suitable enzyme for example, but not limited to the Phusion enzyme (MJ Research, Finland). Typically, a smear of DNA fragments is generated during the amplification reaction (see FIG. 2b).

FIG. 2b shows a typical 'smear' of DNA amplification products. The annealing temperature influences the product size. Depending on the desired fragments-size, PCR conditions can be adjusted accordingly. Usually, an increased annealing/elongation temperature will lead to an increased product size. As larger PCR fragments can cross-hybridize to more of the oligos on the microarray, preferably they are avoided.

After labelling of sample and control samples with an appropriate label, for example, but not limited to a fluorophore such as monofunctional Cy3/Cy5 dyes, the labeled samples may be hybridized to a nucleotide array. In separate embodiments of the present invention, which are not meant to be limiting in any manner, the arrays may comprise human 1.7 k cDNA arrays (UHN/Toronto, Can; which contain 1718 well characterized human ESTs), CpG island arrays (UHN/Toronto, Can), containing 12192 CpG island clones from the Sanger Centre/UK and custom made oligo-arrays for example, but not limited to an array spanning about 100 kb of the human COMT-ARVCF region on chromosome 22 have been successfully employed as arrays in practicing the method of the present invention. The present invention further contemplates the use of any array known in the art in the method of the present invention.

Design of the Oligo-arrays

Without wishing to be limiting in any manner, epigenetic oligo-microarrays may be prepared on CMT-GAPS slides (Corning Inc.) or equivalent pre-processed microarray slides. Oligos for a desired chromosomal region (for example, but not limited to human LINE repetitive elements are preferably about 25 bp to about 50 bp in length or longer. The sequence of the oligos is preferably derived from loci between methylation-sensitive restriction sites used in the method (more preferably AciI, HpaII and Hin6I). The oligos are preferably designed either between each adjacent restriction sites or for every second site, depending on the specificity desired for each chromosomal region.

Figure 5:
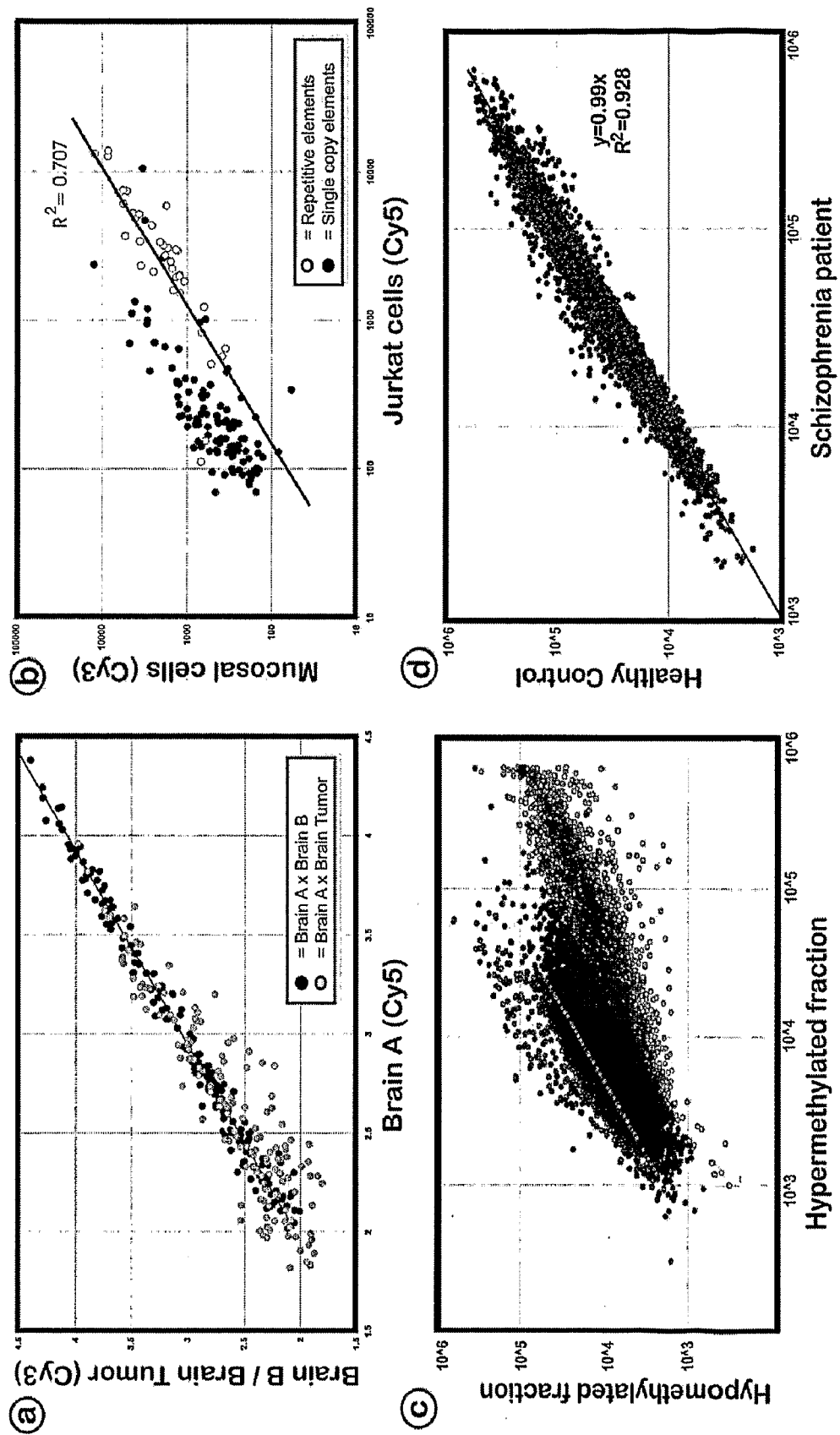
FIG. 5 shows representative results of applying the methods of the present invention to various cell or tissue types.
Figure 7A:
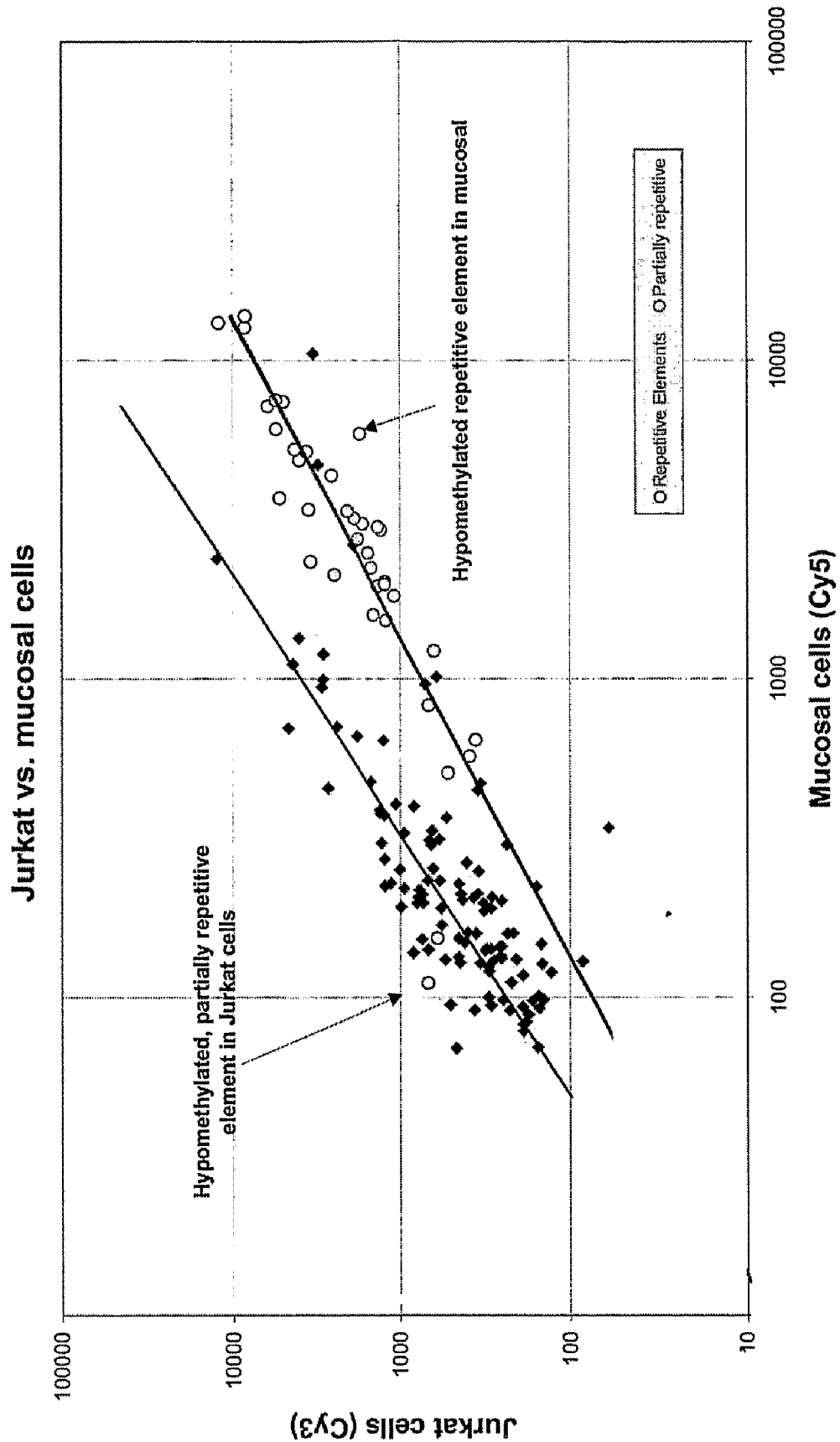
FIG. 7A shows a representative scatter plot of an experiment that detects methylation differences within repetitive elements (e.g. ALU or LINE elements) in different tissues. Grey circles indicate partially repetitive sequences. (about 15 to about 30 copies/genome); while white circles indicate highly repetitive sequences (about >100 copies/genome).

The method of the present invention maybe employed in a wide variety of applications, for example, but not limited to the detection of methylation differences within human repetitive elements in different cell types (FIG. 5b and FIG. 7a).

In FIG. 5b, as an example, DNA from a buccal swab was compared to the DNA from Jurkat cells. The analysis showed that the global methylation level of repetitive elements was not significantly different in the two test samples. In contrast, several loci in the COMT region displayed different levels of methylation, accompanied by increased hypermethylation of this chromosomal region in Jurkat cells.

FIG. 7a shows a representative scatter plot of an experiment that detects methylation differences within repetitive elements (e.g. ALU or LINE elements) in different tissues. Grey circles indicate partially repetitive sequences (about 15 to about 30 copies/genome); while white circles indicate highly repetitive sequences (about >100 copies/genome).

Figure 7B:
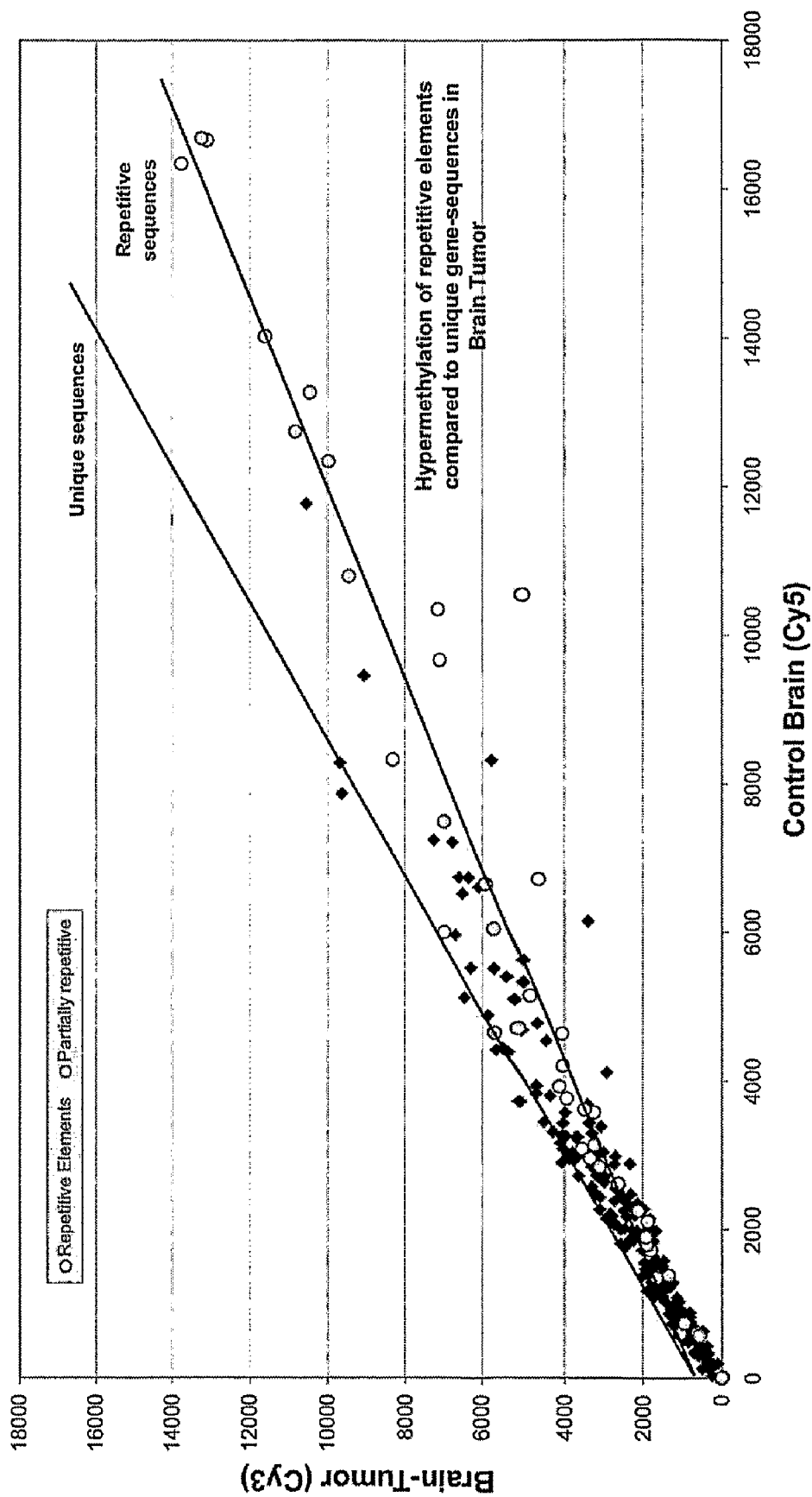
FIG. 7B shows a representative scatter plot of an experiment that detects methylation differences in the unique gene- and intergenic-sequences as well as of repetitive elements in the COMT-ARVCF chromosomal region on human chromosome 22.

The methods of the present invention may also be employed to detect methylation differences in unique genesequences as exemplified for the analysis of brain-tumors compared to control brains (see FIG. 5a and FIG. 7b).

FIG. 7b shows a scatter plot of an experiment that detects methylation differences in the unique gene- and intergenicsequences as well as of repetitive elements in the COMT-ARVCF chromosomal region on human chromosome 22. In this comparison the analysis of the oligo-arrays revealed a relative hypermethylation of repetitive elements in the brain tumor.

In FIG. 5a the COMT oligonucleotide array was used to produce a plot that identifies DNA methylation changes in a brain tumour. In contrast to the pair of non-tumorigenic control DNA samples, where hybridization signals are close to the regression line (indicating similar DNA methylation patterns), a visible proportion of the hybridization signals originating from the unmethylated DNA fraction of the brain tumour deviates from the regression line.

Figure 6:
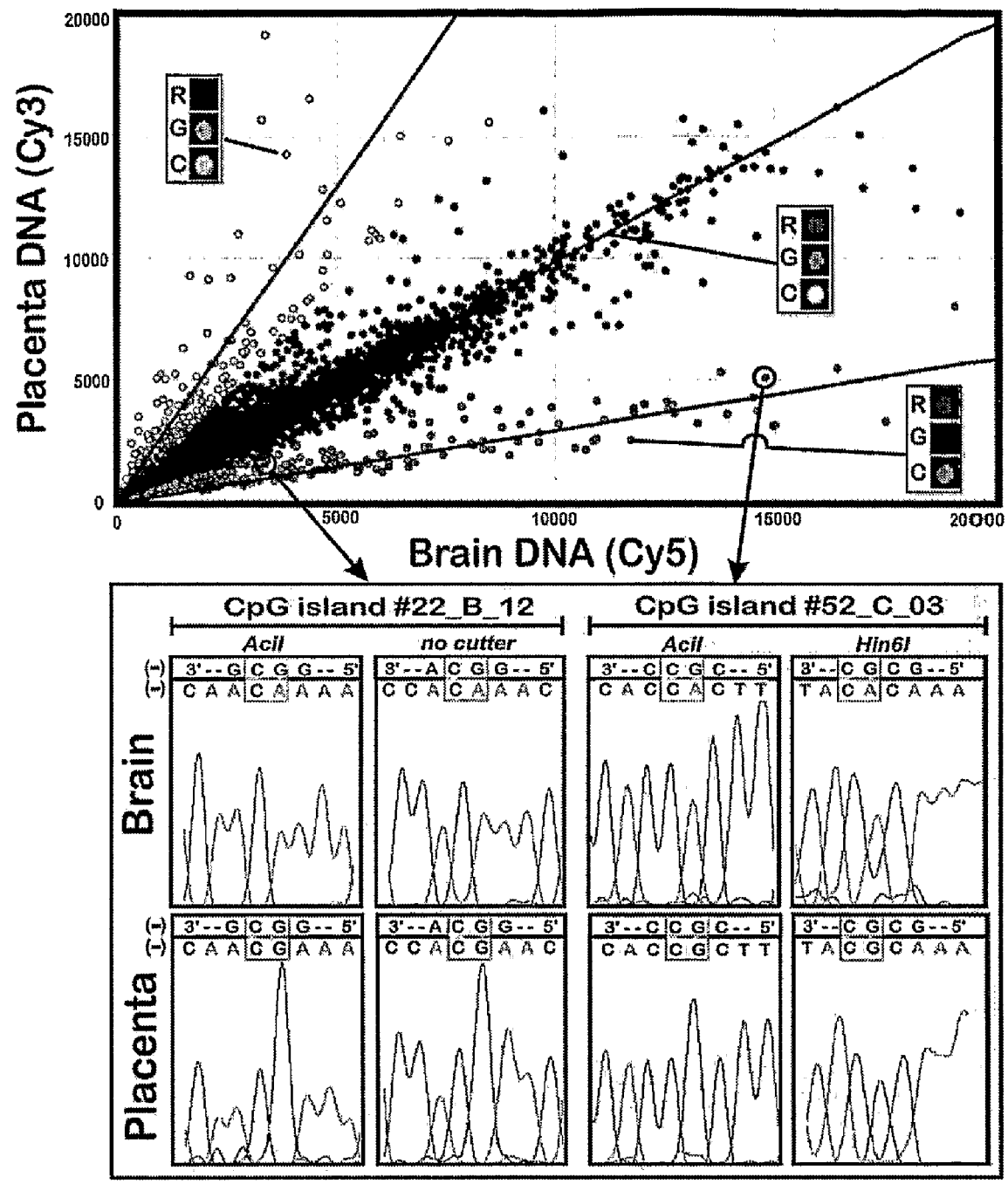
FIG. 6 shows an example of the present invention using a CpG island microarray that contains over 12,000 fragments representing human CpG islands. Hybridization of the unmethylated fraction of placenta DNA and post-mortem brain DNA to a CpG island array. Two pools of CpG island elements could be identified, which display significantly different methylation levels between these tissues. Examples of scanner readings are shown as R=red channel (Cy5), G=green channel (Cy3), C=combination of both channels. To validate the identified methylation differences, several CpG islands were subjected to bisulfite modification based mapping of methylated cytosines as exemplified for CpG island clones 22_B_12 (promoter region of Galectin-1) and 52_C_03 (promoter region of a brain-specific transcript, CR606704). The top sequence shows the reverse strand (−) of the original restriction sites, the bottom sequence displays the bisulfite-modified DNA. For each bisulfite-modified CpG-island, 8 to 10 clones were sequenced per tissue. The strong outlier 52_C_03 revealed a complete methylation in all interrogated CpG's in brain and no methylation in placenta In contrast, clone 22_B_12 showed subtler methylation differences (15-100%), depending on the CpG-dinucleotide.
Figure 9:
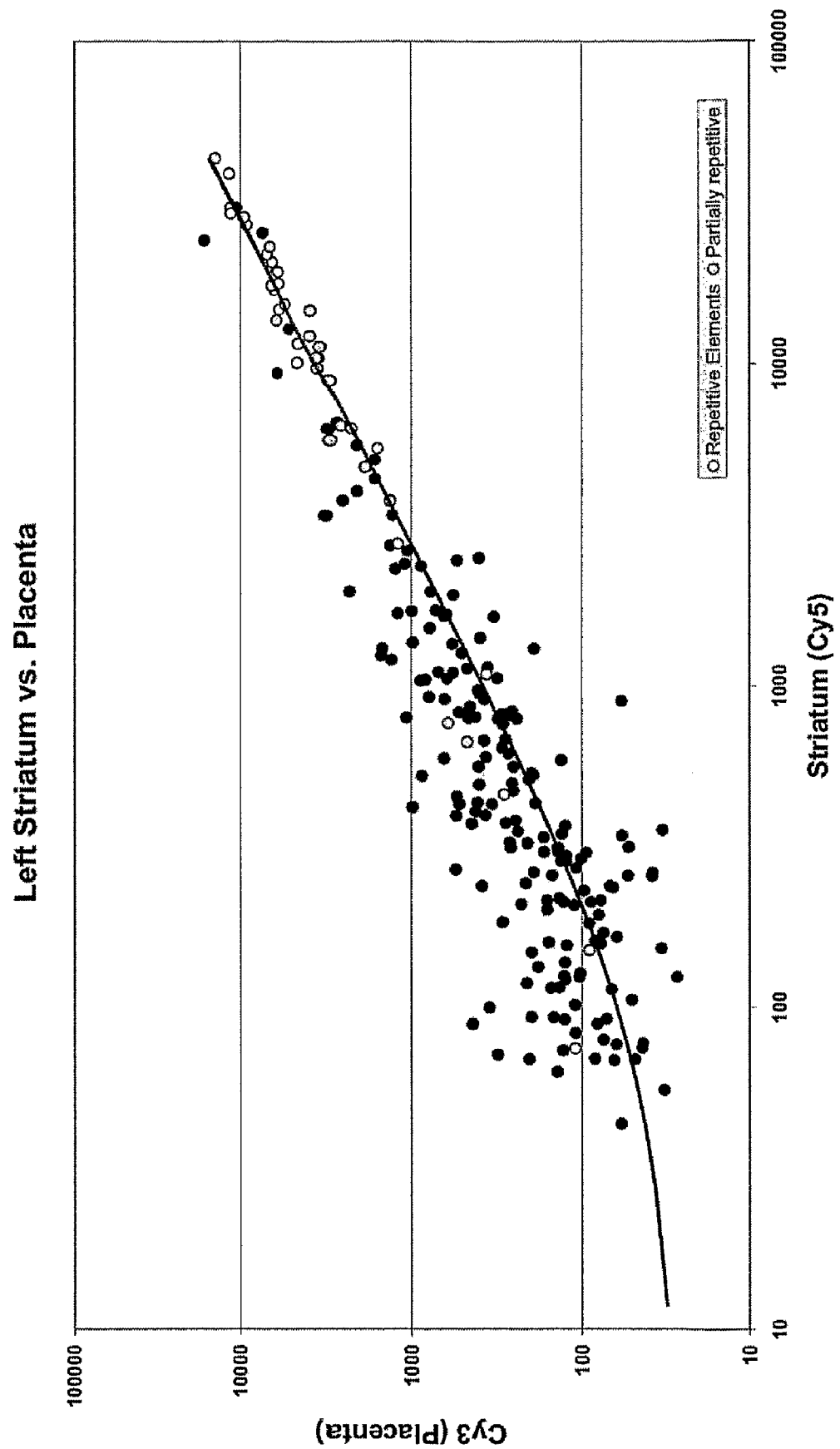
FIG. 9 provides a representative scatter plot illustrating that methylation differences that exist between DNA from human placenta tissue and DNA from post-mortem human striatum tissue.

FIGS. 6 and 9 show examples of applying the method of the present invention to compare different tissues in respect to their methylation profile on chromosome 22. As shown in FIGS. 6 and 9, methylation differences exist between DNA from human placenta tissue and DNA from post-mortem human striatum tissue. The method reveals a significant temporal- and spatial methylation difference between these two tissue types. The further the location of a dot from the regression line, the larger the DNA methylation difference in the given location of the DNA fragment.

Referring specifically to FIG. 6 a representative scatter plot is shown that identifies tissue specific effects as determined using CpG island microarrays that contain 12,192 CpG island clones. CpG islands tend to be found in many promoter sequences and their methylation has profound effects on gene silencing in mammalian genomes. The scatter plot in FIG. 6 shows two distinct spot areas, which represent predominantly hypomethylated fragments in placenta (region indicated by regression line closest to y-axis) and brain (region indicated by regression line closest to x-axis), respectively. About 11% of the CpG island-fragments exhibited 2-fold signal intensity difference between the two tissues. Some of the strongest brain-specific signals could be identified for CpG islands associated with neuronal genes such as DPYSL5, FABP7, DIRAS2, GRIN3A, SLC24A3 or DSCAML1, whereas strong placenta-specific outliers were associated with genes such as PCM1, CCND1, HA-1 or ADAMTSL1. Overall, analysis revealed that brain DNA harbored approximately 2.6× more hypomethylated CpG islands than placenta DNA. In humans, about 70% of all CpG islands are associated with genes24 (56% with promoter regions), therefore it can be expected that a certain percentage of the unmethylated CpG islands are associated with expression of nearby genes. More subtle changes in DNA methylation patterns were identified when post-mortem brain tissues of a healthy individual were comparing with the same tissue from a schizophrenia patient (FIG. 5d).

Methods for analyzing the methylation state of cytosines provide a high throughput approach for profiling of DNA methylation patterns. The possibility to analyze minute amounts of DNA (<10 ng) may enable the epigenetic screening of small DNA amounts, e.g. when DNA is extracted from plasma, serum or other body fluids or in prenatal diagnostics. Although all the examples disclosed herein pertain to human DNA, it will be recognized that the same strategies can be used for epigenetic analyses of numerous other species.

Thus far, 'epigenomic' microarray approaches have been based on the enrichment of the hypermethylated DNA and predominantly used for identification of abnormally methylated CpG islands in malignant cells. Although this strategy seems to be useful for detection of major epigenetic changes in some regions of the genome, the overall proportion of the interrogated CpG sites is substantially lower in comparison to the approach based on the analysis of the unmethylated fraction. As shown in Example 1, interrogation of the unmethylated fraction of genomic DNA may be up to several hundredfold more efficient in comparison to the hypermethylated fraction scenario. Furthermore, since unmethylated cytosines represent a much smaller part of cytosines in comparison to the methylated one (depending on the tissue, 70%-90% of cytosines are methylated), analysis of this smaller unmethylated fraction of genomic DNA is more sensitive to detect subtle changes. For example, an increase of 10% from the normal density of metC would result in 100% (from 20% to 10%) difference in the unmethylated fraction, but only 12% (from 80% to 90%) in the hypermethylated fraction of genomic DNA.

Profiling of DNA methylation, as contemplated in the present invention, can be implemented in a systematic, unbiased fashion that is not limited to the traditionally preferable regions such as CpG islands. Outside the CpG islands, there are numerous other genomic loci that may be the sites for differential epigenetic modification, for example, without limitation, enhancers, imprinting control elements or the regions encoding intron-specific snoRNAs.

The methods of the present invention can be of significant benefit in the identification of inter-individual variation, identification of epigenetic changes during tissue differentiation and differences across species, and understanding of epigenetic effects of various environmental factors, among numerous others developments. Of particular interest is the application of the high throughput DNA methylation analyses to addressing the molecular basis of various non-Mendelian irregularities of complex diseases, such as discordance of monozygotic twins, remissions and relapses of a disease, parent of origin- and sex-effects, tissue and site specificity.

The above description is not intended to limit the claimed invention in any manner, furthermore, the discussed combination of features might not be absolutely necessary for the inventive solution.

The present invention will be further illustrated in the following examples. However it is to be understood that these examples are for illustrative purposes only, and should not be used to limit the scope of the present invention in any manner.

EXAMPLES

Example 1

Large Scale Profiling of DNA-methylation in a Variety of Genetic Elements, Cell Types, Tissues, and Test Subjects Example 1 presents a comprehensive microarray-based high throughput technology for DNA methylation profiling of DNA regions that span from hundreds of kilobases to megabases and could be applied to the entire human genome. The approach is based on the enrichment of differentially methylated fractions of genomic DNA and the subsequent interrogation of these fractions on high-density DNA microarrays. Some microarray-based technologies used for epigenetic analyses are already available, however, below is a series of alternative and new aspects, such as focusing on the unmethylated (instead of the hypermethylated) fraction of genomic DNA and parallel detection of confounding effects of DNA sequence variation, among others.

Enrichment of the Unmethylated Fraction of Genomic DNA

The schema for enrichment of unmethylated portions of the genome is presented in FIG. 1. Genomic DNA is digested with methylation-sensitive restriction enzymes (FIG. 1, middle panel). Whereas methylated restriction sites remain unaltered, the sites containing unmethylated cpGs are cleaved by the enzymes, and DNA fragments with 5'-CpG protruding ends are generated. The proportion of interrogated CpG sites depends on the methylation sensitive restriction enzymes used for the restriction of DNA. Based on an analysis (data summarized in Table 1) of the CpG dinucleotides within the sites of methylation sensitive restriction enzymes across several megabases of human genomic DNA, the combination of three enzymes, HpaII Hin6I, and AciI, should interrogate ~32% of all CpG dinucleotides in mammalian DNA. The addition of two other relatively inexpensive methylation-sensitive CpG-overhang generating enzymes, HpyCH4IV and Hin1I, would theoretically increase the proportion of interrogated CpGs to ~41%. Depending on the array-type, either a single cutter or a 'cocktail' of about 2, 3, 4, 5, or more restriction enzymes may typically be used.

The application of a set of enzymes might be disadvantageous for the analysis of GC-rich regions as such a strategy would produce restriction fragments too short for an efficient hybridisation. In the latter case, it is preferable to use a smaller number of restriction enzymes. Based on experimental results and on a computer-based analysis of 100 randomly picked CpG islands and non-CpG island regions in the human genome, the most suitable restriction enzymes for CpG-island analysis are Hin6I or HpaII, followed by AciI, and Hin1I (Tab. 1). In contrast, for regular DNA sequences, double- or triple-digest combinations of AciI, HpaII, HpyCH4IV and Hin6I may be preferred.

TABLE 1

Enzymes that generate protruding ends in the restriction fragments, which are complementary to the adaptor U-CG1, TA-1 and AATT-1. Asterisk (*) indicates the number of 75 bp-2 kb long ('informative') fragments, derived from several Mbp of randomly selected CpG island and non-CpG island sequences on chromosomes 1, 2, 4, 5, 6, 9, 17, 19 and 20.

| Enzymes | % coverage of CpGs in λ DNA | % coverage of CpGs in human gDNA | # of fragments (per kb) in CpG islands* | # of fragments in non-CpG islands* |
|---|---|---|---|---|
| HpaII (BsiSI) | 10.5% | ~8.6% | 3.98 | 1.18 |
| Hin6I (HinP1I) | 6.9% | ~6.4% | 3.98 | 0.61 |
| AciI (SsiI) | 16.6% | ~17.4% | 3.23 | 1.79 |
| Hin1I (AcyI, BsaHI) | 0.1% | ~2.0% | 1.92 | 0.11 |
| HpyCH4IV | 4.6% | ~6.6% | 1.31 | 1.08 |
| Bsu15I (ClaI, BspDI) | 0.5% | ~0.2% | <0.01 | 0.02 |
| NarI (MlyI) | <0.1% | ~0.6% | 1.08 | <0.01 |
| Bsp119I (AsuII, CbII) | 0.2% | ~0.1% | 0.11 | <0.01 |
| BstBI (FspII) | 0.2% | ~0.1% | 0.11 | <0.01 |
| Psp1406I (AclI, PspI) | 0.2% | ~0.3% | <0.01 | 0.05 |
| XmiI (AccI) | 0.3% | ~0.1% | 0.19 | 0.34 |
| TasI | | na | 0.80 | 2.88 |
| Csp6I | | | 2.23 | 1.41 |
| MseI | | | 0.80 | 2.88 |
| BfaI | | | 1.56 | 1.55 |

After the digestion of genomic DNA, the double-stranded adaptor U-CG1 is ligated to the CpG-overhangs. At this point, it is expected that most of the relatively short and amplifiable DNA fragments derive from the unmethylated DNA regions. Some ligation fragments, however, may still contain metCpG. A proportion of such fragments can be eliminated by treatment with McrBC, which cleaves DNA containing metC and will not act upon unmethylated DNA. McrBC restriction sites consist of two half-sites of the form (G/A) metC, which can be separated by up to 3 kb 19, 20. Hence, as can be seen in FIG. 2C, a proportion of DNA fragments with 2 or more (G/A)metC within the restriction fragment is cleaved and therefore deleted from the subsequent enrichment steps. The remaining pool of unmethylated DNA fragments is then enriched by aminoallyl-PCR amplification that uses primers complementary to the adaptor U-CG1. The accuracy of the adaptor-amplification approach is illustrated by selective amplifications of 1 phage fragments from the mixture with human DNA (FIG. 2A).

An advantage of using protruding ends in the adaptor ligation step is that degraded DNA fragments will not be ligated and amplified, and therefore will not interfere with the methylation analysis. FIG. 2a also demonstrates that the enrichment of DNA fragments depends on their length (large, CpG poor fragments are not amplified), and furthermore that the preferential amplification of specific size fragments is highly reproducible.

Comparison of Unmethylated/Hypomethylated Fraction to Methylated Fraction

Most of the previous microarray-based epigenetic studies target the hypermethylated DNA sequences; however, although a valid approach, interrogation of the unmethylated fraction is much more informative. For example, in the 100 kb region of chr 22 (COMT, see the Microarray Design section below), which contains 2,193 methylatable cytosines enrichment of the unmethylated fraction would theoretically generate approximately 401 amplicons of sufficient size ($\geq 50$ bp), each representing the methylation status of at least one cytosine. In contrast, the combination of MseI (+BsuI, to remove unmethylated fragments), the most frequently used enzymes for enrichment of the hypermethylated fraction, would produce 227 amplicons. Seventy-seven amplicons would either contain no CpG dinucleotides or they would be too short to hybridize stringently to a microarray. Of the remaining 150 fragments, 144 contain multiple CpGs; hence, they are not fully informative since a single unmethylated restriction site would eliminate the entire fragment from the eventual amplification. Overall, only six of the 2,193 methylatable cytosines are truly informative, and none of these CpG dinucleotides are targeted by BsuI. In experiments with the microarrays types, PCR products from the unmethylated fraction produced strong signals (signal to noise ratio >6) for up to 98% of all arrayed clones/oligos, whereas the hypermethylated fraction produced fewer signals (up to 86%). On average, the unmethylated fraction detected approximately 18% more spots. Computer-based analysis of 50 randomly picked CpG island sequences revealed that, for example, the unmethylated fraction derived from HpaII cleavage results in approximately 22 times more fragments (19.9 fragments/kb) of the appropriate size range (75-2,000 bp) than the hypermethylated fraction (0.9 fragments/kb) using MseI.

Nevertheless, analysis of the hypermethylated DNA fraction may also add some new information to the methylation profiles. Thus, a method of enrichment of methylated sequences is disclosed herein (FIG. 1 right panel). This enrichment method comprises cleavage with the 4-basepair frequent cutters, for example, TasI (AATT/) and/or Csp6I (G/TAC). As another example, BfaI or MseI can be used in combination with the Csp6I-specific adaptor. All four enzymes are relatively inexpensive and produce DNA fragments in mammalian genomes of an average length of about 400 bp to about 750 bp. The recognition sequences of TasI and Csp6I are infrequent within GC-rich regions, leaving most CpG-islands intact. The analysis of 50 randomly picked CpG islands and several megabases of different chromosomes revealed that a digest with Csp6I would produce more informative fragments in CpG islands than a digest with MseI, whereas TasI and MseI produce informative fragments preferentially in DNA regions outside of CpG islands (Table 1). After ligation to the AATT- and TA-overhang specific adaptors "AATT-1" and "TA-1", the un- and hypo-methylated ligation products are eliminated from the reaction by cleavage with a cocktail of methylation-sensitive restriction enzymes such as HpaII, HhaI (Hin6I), HpyCH4IV, HinII and AciI. Compared to a single digestion with BstUI, a cocktail of restriction enzymes will delete a higher percentage of unmethylated sequences from the DNA fraction and furthermore, no pre-selection of CpG island clones that contain BstUI sites is required. The remaining pool of mostly hypermethylated DNA fragments is then enriched by the aminoallyl-PCR amplification as described for the hypomethylated fraction and finally hybridized to a microarray (FIG. 5C).

Microarray Design

Figure 3:
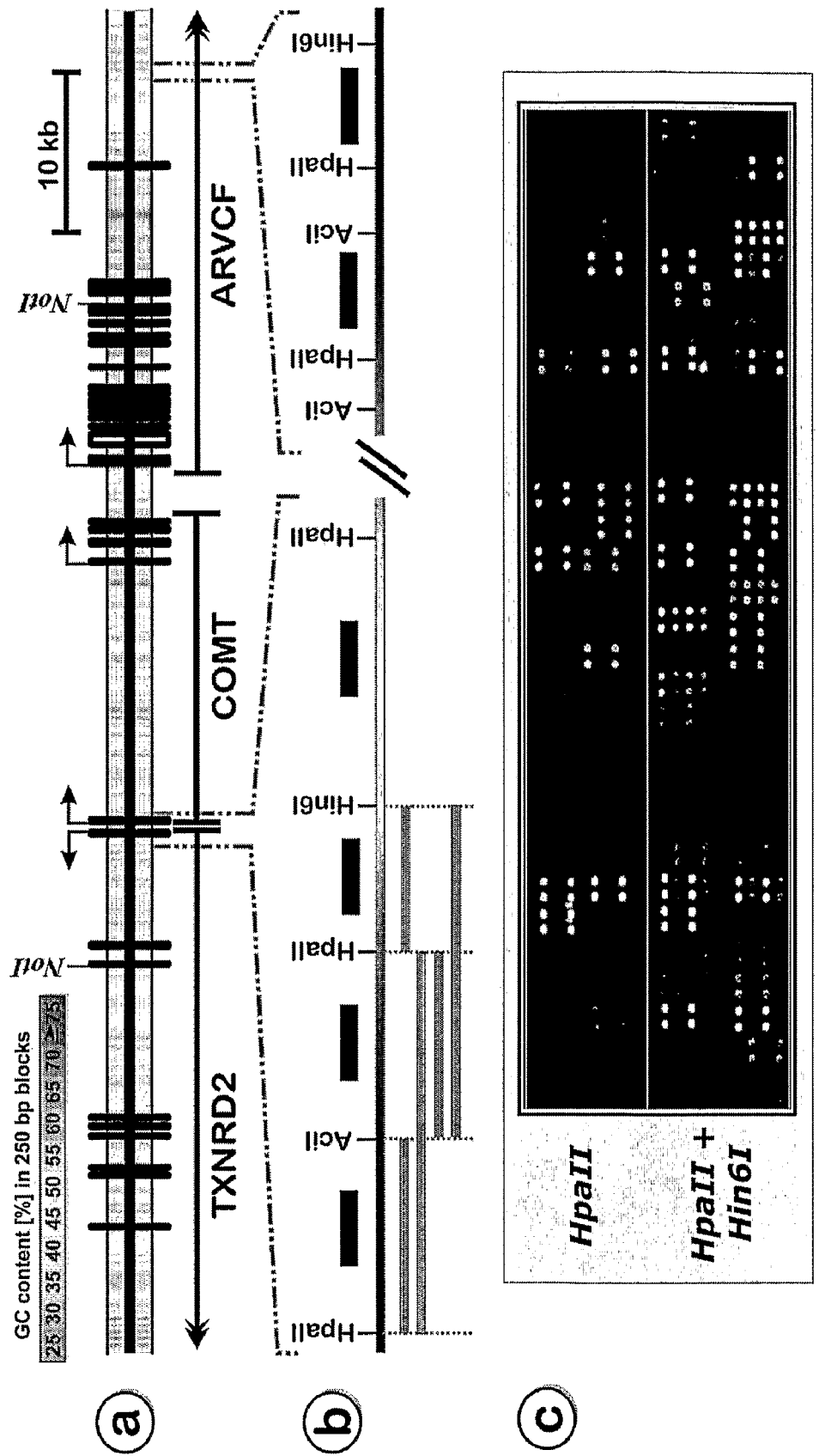
FIG. 3 shows another example of a method of the present invention that provides for DNA methylation analysis of the 100 kb COMT region.

Various aspects of the microarray-based DNA modification profiling were investigated on the oligonucleotide-microarray that interrogates an approximately 100 kb fragment on chromosomal region 22q11.2 (FIG. 3a). This chromosomal region contains the gene encoding the catechol-O-methyltransferase (COMT), and also the thioredoxin reductase 2 gene (TXNRD2) and the armadillo repeat gene deleted in velocardiofacial syndrome (ARVCF). For maximal informativeness, it is preferable to design oligonucleotides according to the restriction sites of the methylation sensitive endonucleases used for the treatment of genomic DNA (FIG. 3b). For the COMT array, 384 oligonucleotides were designed, each 50 nucleotides long, representing every restriction fragment flanked by HpaII, Hin6I, and AciI restriction sites. In addition, control DNA fragments containing lambda phage, pBR322, PhiX174, pUC57, and Arabidopsis sequences were spotted on the array. Additionally, 12,192 element containing CpG island- and high-density chromosome 21/22-microarrays were used.

Reproducibility

Figure 4:
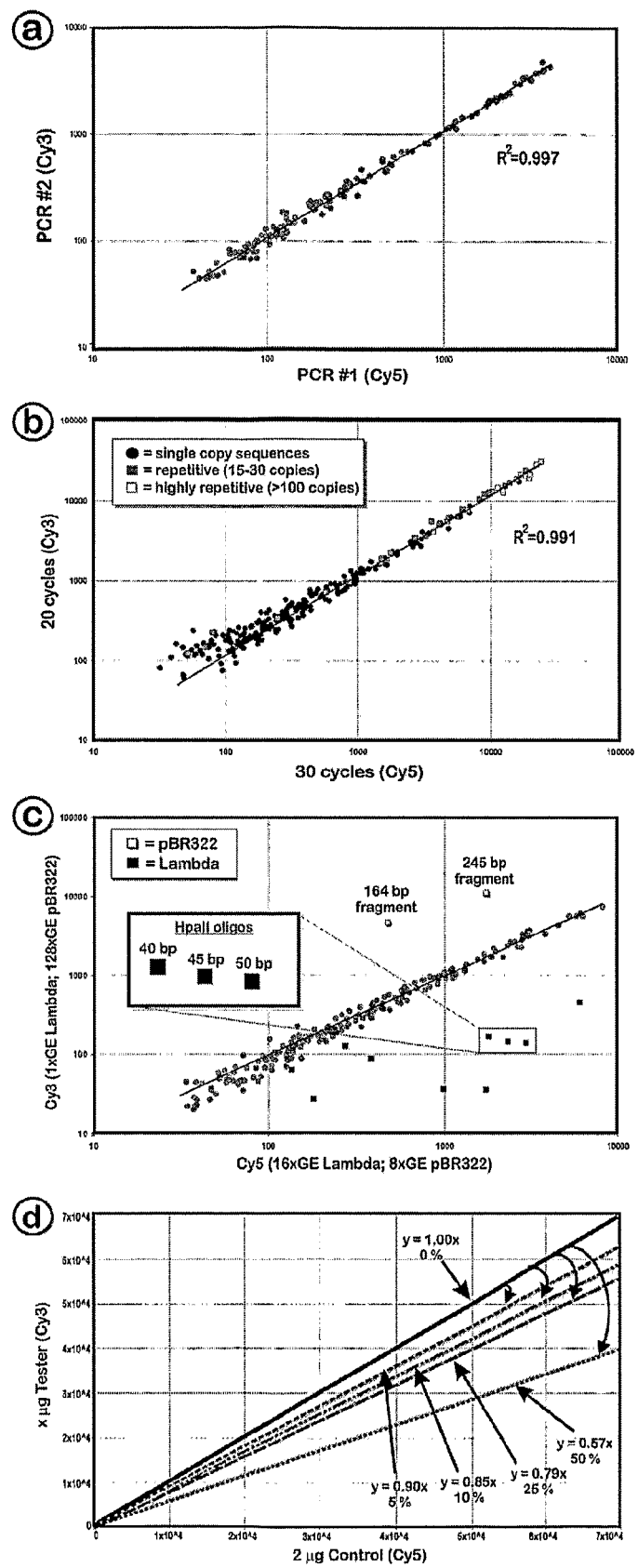
FIG. 4 shows the reproducibility and sensitivity of a method of the present invention with respect to the COMT region.

To test the reproducibility of the methods of the present invention, a genomic DNA sample was split and subjected to the procedure of enrichment of the unmethylated fraction. The resulting amplification products generated were labelled with Cy5 and Cy3 and then co-hybridized on the COMT array, which contains probes that flank the HpaII, Hin6I and AciI restriction fragment around the COMT gene. The Cy3 and Cy5 hybridization intensities exhibited very similar values (R2=0.997; FIG. 4A). Analogous experiments, including switch dye hybridizations, were repeated several times also with the CpG island arrays and in all cases were highly reproducible (R2>0.97).

Controlling Sequence Specific Biases During Amplification of DNA

The rate of amplification of repetitive sequences generally declines faster than that of less abundant fragments in the later cycles of PCR. With increasing amplification cycles, repetitive DNA strands reach relatively high concentration and may begin re-annealing to each other during the steps below the DNA melting temperature. To avoid this, a two-temperature PCR that uses a combined high-temperature elongation-annealing step was applied. A series of experiments were performed investigating how the number of PCR cycles would affect the hybridization patterns. As can be seen in FIG. 4B, the relative intensities of the hybridization signals of both, single copy sequences and repetitive DNA fragments, were similar in the range of 20 to 30 amplification cycles (R2=0.991). Only, when increasing the cycle numbers beyond 40 cycles, a biased amplification of some DNA sequences was observed (data not shown).

Sensitivity

To test if differentially represented DNA fragments in two different DNA samples can be detected by this method, human genomic DNA was 'spiked' with unmethylated heterologous DNA, Lambda phage and pBR322 plasmid (FIG. 4C). The amount of Lambda and pBR322 corresponded to the increasing numbers of human genomic equivalents (1 GE of 'spike' DNA equals 16.28 picogram of Lambda/microgram of gDNA and 1.45 picogram/microgram gDNA of pBR322, respectively). Hence, each of the experiments compared the intensities generated by 1 GE of Lambda plus 128 GE of pBR322 (Y axis) versus 16 GE of Lambda plus 8 GE of pBR322 (X axis). While the plotted signal intensities of the human genomic DNA sequences are positioned on or close to the regression line, the Lambda and pBR322 fragments were identified as outliers. The average signal intensity ratio of Lambda oligonucleotides was 15.4, which is very close to the ratio of spiked DNA (16:1). The intensity values for pBR322 were not as linear and exhibited a 6.5-10 fold difference (expected the same ratio of 1:16), most likely due to saturation effects during the hybridization.

In order to determine the sensitivity of the hybridization per se, a control amplicon DNA was compared to itself but by decreasing the amounts of DNA by 5%, 10%, 25% and 50%. On the global level, the regression lines [y=f(x)] reproducibly reflected the differences of the amount of amplicon DNA used in the hybridization and varied by 5%-7% from the expected values (FIG. 4D). As expected, individual sites exhibited a lower degree of precision, and the accuracy depended on the signal intensity, i.e. the stronger the signal, the closer the observed spot intensity to the expected one was. The rates of false outliers (log-ratio <-0.3; >0.3) were approximately 3% and 1%-15% for the CpG island arrays and COMT oligonucleotide arrays, respectively. Usually, replication of microarray experiments reduced the degree of aberration (log-ratio <-0.3; >0.3) below 2% for all types of microarrays.

Examples of Applying DNA Methylation Analysis

Identification of DNA methylation differences is provided in a series of examples below. The COMT oligonucleotide array was used to identify DNA methylation changes in a brain tumour (FIG. 5A). In contrast to the pair of non-tumorigenic control DNA samples, where hybridization signals are close to the regression line (indicating similar DNA methylation patterns), a visible proportion of the hybridization signals originating from the unmethylated DNA fraction of the brain tumour deviates from the regression line.

Another application of the technology includes epigenetic profiling of different tissues. As an example, DNA from a buccal swab was compared to the DNA from Jurkat cells (FIG. 5B). The analysis showed that the global methylation level of repetitive elements was not significantly different in the two test samples. In contrast, several loci in the COMT region displayed different levels of methylation, accompanied by increased hypermethylation of this chromosomal region in Jurkat cells.

A second example of tissue specific effects was shown on the CpG island microarrays that contain 12,192 CpG island clones. CpG islands tend to be found in many promoter sequences and their methylation has profound effects on gene silencing in mammalian genomes. The scatter plot shows two distinct spot areas, which represent predominantly hypomethylated fragments in placenta (regression line closest to y-axis) and brain (regression line closest to x-axis), respectively (FIG. 6). About 11% of the CpG island-fragments exhibited 2-fold signal intensity difference between the two tissues. Some of the strongest brain-specific signals could be identified for CpG islands associated with neuronal genes such as DPYSL5, FABP7, DIRAS2, GRIN3A, SLC24A3 or DSCAML1, whereas strong placenta-specific outliers were associated with genes such as PCM1, CCND1, HA-1 or ADAMTSL1. Overall, analysis revealed that brain DNA harboured approximately 2.6× more hypomethylated CpG islands than placenta DNA. In humans, about 70% of all CpG islands are associated with genes (56% with promoter regions), therefore it can be expected that a certain percentage of the unmethylated CpG islands are associated with expression of nearby genes.

More subtle changes in DNA methylation patterns were identified when post-mortem brain tissues of a healthy individual were compared with the same tissue from a schizophrenia patient (FIG. 5D).

Verification of Detected Methylation Differences

Several loci that displayed methylation differences in our experiments were selected for verification by the sodium bisulfite modification mapping of methylated cytosines. The technique is based on the reaction of genomic DNA with sodium bisulfite under conditions such that cytosine is deaminated to uracil but 5-methylcytosine remains unreacted. In the sequencing of amplified products, all uracil and thymine residues are detected as thymine and only metC residues remain as cytosine. The sites for the methylation-sensitive restriction enzymes used in our experiments showed the expected methylation difference across the DNA samples, as exemplified for CpG island clones located in the promoter region of galectin-1 and in the promoter region of a brain-specific transcript CR606704 (FIG. 6) Both CpG island sequences displayed methylation differences between brain (unmethylated) and placenta (methylated). It is interesting to note that the differences were not limited to CpG dinucleotides within the restriction sites. In most cases, the methylation-patterns at the enzyme-sites also reflected the methylation patterns of the surrounding CpGs.

Large-scale Fine Mapping of Methylation Differences

Analysis of the unmethylated fraction from brain specific DNA of 8 adults using a chromosome 21/22 tiling array detected 488 to 747 hypomethylated sites per sample. This number increased to 977 in a merged map, showing that many sites were common between different individuals. The vast majority of the sites (approximately 90%) lied outside of the 5' ends and 5' flanking regions of the genes consistent with abundant transcriptional activity and a significant fraction of transcription factor binding sites found outside of known annotations.

The unmethylated sites outside of the 5' ends of known genes were about equally distributed between sites residing within introns of known genes and outside of the gene boundaries. Interestingly, while some genes, like BCR on chromosome 22, showed a large number of sites inside the gene boundaries, some loci, like ADARB1 spanning approximately 150 kb of chromosome 22, were essentially devoid of internal unmethylated sites and in some cases, such as the SIM2 locus, the detected unmethylated sites were limited to the first intron (FIG. 7A-C). This observation suggests a non-random distribution of unmethylated sites. Overall, unmethylated sites detected in this study cover approximately 0.47 Mbp or approximately 4% of the 12 Mbp of non-repetitive sequences of chromosomes 21 and 22 interrogated in the combined map of all 8 individuals with an average of 0.28 Mbp or 2.3% in any given individual.

Detection of Confounding Effects of DNA Sequence Variation

Since restriction enzymes are used in the enrichment of differentially modified DNA fractions, DNA sequence variation may simulate epigenetic differences. However, until now, microarray methods used in epigenetic studies have not been differentiating between methylation changes and the presence of SNPs within the restriction sites of the applied restriction enzymes. An approach for excluding the impact of DNA sequence variation, is to check the available SNP databases in order to identify the DNA sequence variation within the restriction sites of the used enzymes. For example, our 100 kb COMT array contains a total of 273 SNPs out of which 101 (37%) reside within CpG dinucleotides and 55 (20%) SNPs are located within the restriction site of the four main enzymes, HpaII, Hin6I, AciI, and HpYCH4IV, which are used to interrogate the methylation patterns. See the SNPper web-based tool available at snpperDOTchipDOTorg, wherein "DOT" is ".". The majority of these CpG-SNPs were located in AciI and HpaII restriction sites, whereas Hin6 and HpyCH4IV sites contained fewer polymorphisms (data not shown).

Another example of an approach to differentiate the DNA sequence effects from the genuine epigenetic differences consists of performing an equivalent microarray experiment on the DNA that is stripped of all methylated cytosines (FIG. 8). Phi29 DNA polymerase is used to amplify whole genomic DNA, which creates a copy of the genome with all methylated cytosines replaced by unmethylated cytosines. Amplified sample-control DNA pairs are then subjected to the same steps as depicted in FIG. 1 and co-hybridized on the microarrays. In the resultant scatter plot of this experiment, outliers are considered to be a result of the nucleotide polymorphisms within the restriction sites of the enzymes used. Furthermore, this data can be plotted against the DNA methylation data, which are assayed in parallel (FIG. 8). In six experiments that used amplified DNA, the number of SNP-based outliers (threshold log-ratio $<-0.3$, $>0.3$) ranged from 272 to 741 (432±165, mean±SD), or 2.2%-6.1% of 12,192 CpG islands. Out of these SNP outliers, 72 to 234 (120±66, mean±SD) were initially identified as DNA methylation differences in microarray experiments using the unmethylated fraction derived from the triple-digest with HpaII, AciI and Hin6I (FIG. 8). From the CpG island array studies, our estimate is that 10% to 30% of the outliers detected in DNA methylation experiment could be due to DNA sequence variation.

Microarray Fabrication and Data Processing

COMT and CpG island microarrays were printed on Corning CMT-GAPSII slides (Corning Life Sciences, Acton, Mass.) using a "VersArray ChipWriter Pro Systems" (Bio-Rad Laboratories, Hercules, Calif.). For the COMT array, we designed 384 oligonucleotides (Operon/Qiagen, US), each 50 bases long, representing every restriction fragment flanked by HpaII, Hin6I, and AciI restriction sites. In addition, control DNA fragments containing Lambda phage, pBR322, PhiX174, and pUC57 sequences were spotted on the array. Each oligonucleotide was diluted to a 25 microMolar solution and spotted four times to give a total of 1,536 spots of chromosome 22. In addition, 192 blank spots consisted of SSC buffer and 48 spots contained Arabidopsis clones. The human CpG island array contains 12,192 sequenced CpG island clones derived from a CpG island library that was originally created with MeCP2 DNA binding columns.

Hybridized arrays were scanned on a GenePix 4000A scanner (Axon Instruments, Union City/Calif., USA) and analyzed using the GenePix 6.0 software. The GenePix PMT voltage for Cy3 and Cy5 channels were balanced with the histogram feature of the scanner software to ensure a similar dynamic range for the two channels. Final scans were taken at 10 micromolar resolution, and images for each channel were saved as separate 16-bit TIFF files. The emission signals for each channel were determined by subtracting the local background from its corresponding median average intensity. These raw data were either exported into a custom Excel spreadsheet for subsequent data analysis or directly imported into the Acuity 4.0 software (Axon Instruments). The resulting datasets were normalized for the normalization features (spike-DNAs) and for signal intensity (Lowess normalization).

Profiling of hypomethylated sites in the brain tissue of 8 adults was carried out using a tiling array spanning approximately 12 Mb of non-repetitive sequence of the distal ⅓ (approximate) of chromosome 21 and ⅓ (approximate) of the proximal portion of chromosome 22 with probes spaced on average every 35 bp center-to-center. The genomic DNA from these individuals was cut with HpaII and Hin6I, without the McrBC treatment, amplified and hybridized to the microarray. Total genomic DNA, not enriched for unmethylated regions, was used as control. Unmethylated sites were defined using a two-step analysis approach essentially identical to the one used to determine transcription factor binding sites in the ChIP-chip assay described in Cawley et al [Cawley S et al. (2004) Unbiased mapping of transcription factor binding sites along human chromosomes 21 and 22 points to widespread regulation of noncoding RNAs. Cell 116, 499-509]. First, a smoothing-window Wilcoxon approach was applied to generate a p-value graph for each individual where probe signal from the enriched fraction was compared to the total genomic DNA in a one-sided upper paired test. The window used in this report was 501 bp. Second, three thresholds were applied to determine the bounds of the unmethylated site: individual probe threshold of $p<10^{-4}$ to determine if a probe is significantly enriched in the unmethylated fraction compared to the control total genomic DNA; maximum distance between the two positive probes=250 bp and minimal size of a site=1 bp. All coordinates and annotation analysis was done on the April 2003 version of the genome.

Methyl-sensitive Digestion of gDNA

Prior to treatment with restriction enzymes, genomic DNA was supplemented with "spike"-DNAs (different concentrations of lambda and Arabidopsis fragments), which were used as controls for signal normalization. For enrichment of the unmethylated fraction, depending on the number of CpG dinucleotides to be interrogated, several combinations of methylation-sensitive enzymes, HpaII, Hin6I, AciI and HpyCH4IV, were used. Genomic DNA was cleaved with a cocktail of these enzymes (10 U/microliter in 2×Y+/Tango buffer, Fermentas Life Sciences/Lithuania) for 8 h at 37° C. to generate fragments with a protruding 3'-GC-5' overhang. For enrichment of the methylated fraction, genomic DNA was cleaved by TasI or Csp6I (10 U/microliter in G+-buffer, Fermentas) for 8 h at 65° C. (TasI) or at 37° C. (Csp6I). Both enzymes target 4-base recognition sequences outside of CpG dinucleotides, thereby producing sticky 5'-AATT-3' or 3'-AT-5' ends, respectively. After the restriction reaction, TasI was inactivated by 0.5 M EDTA.

Adaptor-Ligation

For the ligation step, genomic DNA was supplemented with 8 GE MspI-cleaved pBR322 plasmid (1 GE=1.45 pg/microgram gDNA), which was used as control for a potential ligation bias. The ends of the cleaved DNA fragments were ligated to the unphosphorylated adaptors. Our adaptors contained a sequence-specific protruding end, a non-target homologous core sequence, a specific antisense-overhang that prevents tandem repeat formation and blunt-end ligation, a 'disrupter' sequence that interrupts the original restriction sites after ligation, a new non-palindromic Alw26I (BsmAI) restriction site that enables the blunt-end cleavage of the adaptor from the target sequences (e.g. for library enrichment) and a non-5'-complementary end.

The CpG-overhang specific universal adaptor "U-CG1" for the unmethylated DNA fraction ligates to DNA fragments generated by 11 methylation-sensitive restriction enzymes HpaII, Hin6I (Hinp1I), HpyCH4IV, Bsu15I (ClaI, BspDI), AciI (SsiI), Psp1406I (Ac1I), Bsp119I (AsuII), Hin1I (AcyI, BsaHI), XmiI (AccI), NarI, BstBI (FspII) and the methyla tion-insensitive enzymes TaqI and MspI. The adaptor represents the annealing product of the two primers:

```
U-CG1a:
5'-CGTGGAGACTGACTACCAGAT-3',        SEQ ID NO: 1;

U-CG1b:
5'-AGTTACATCTGGTAGTCAGTCTCCA-3',    SEQ ID NO: 2
```

The AATT-overhang specific adaptor "AATT-1" for the methylated DNA fraction fits to DNA ends produced by the restriction enzyme TasI (TspEI), whereas the "TA-1" adaptor fits to ends produced by Csp6I, BfaI or MseI respectively:

```
AATT-1a:
5'-AATTGAGACTGACTACCAGAT-3',        SEQ ID NO: 5;

AATT-1b:
5'-AGTTACATCTGGTAGTCAGTCTC-3',      SEQ ID NO: 6;

TA-1a:
5'-TATGAGACTGACTACCAGAT-3',         SEQ ID NO: 7;

TA-1b:
5'-AGTTACATCTGGTAGTCAGTCTCA-3',,    SEQ ID NO: 8.
```

All adapters were prepared by mixing equimolar amounts of the primer pairs, incubating the mixture at 80° C. for 5 min, and then cooling it down to 4° C. with 1° C./min. The double-stranded adaptors [200 pmol/microliter] were added at 0.1 pmol per enzyme for each ng of the cleaved DNA (e.g. 0.3 pmol/ng in a triple-digest HpaII/Hin6I/AciI). The ligation-mixture with 400 ng template DNA was supplemented with 2 microliter of 10× ligation buffer (Fermentas), 1 microliter ATP [10 mM], and water to 18 microliter. The reaction was started in a thermal-cycler at 45° C. for 10 min, chilled on ice and 2 microliter T4 ligase (Fermentas) was added. The ligation reaction was carried out at 22° C. for 18 h, followed by a heat-inactivation step at 65° C. for 5 min. The mixture was then cooled down to room temperature with 1° C./min and stored at 4° C. for subsequent procedures.

Methylation-specific Cleavage of Ligation Products

Unmethylatedfraction: in order to delete internally methylated ligation fragments, the ligation products were treated with McrBC (NEB) for 8 h at 37° C. in a mixture containing 2 mM GTP (supplied with McrBC), 1× BSA, 10 U/microgram McrBC and NEB buffer 2 and stored at 4° C. To control for McrBC activities, the DNA mixture was supplemented with 8 GE pUC57 plasmid (1 GE=0.9 pg of pUC57 corresponds to 1 microgram gDNA) that was cut with HpyCH4VI, ligated to the adaptor and methylated with SssI-methylase. Methylated fraction: to delete internally unmethylated ligation-fragments, the ligation products were cut with methylation-sensitive restriction enzymes HpaII, Hin6I, AciI or HpyCH4IV. Ligation products were incubated for 8 h at 37° C. in a mixture containing 10 U/microgram HpaII, 6 U/microgram Hin6I and 8 U/microgram AciI in 2×Y+/Tango buffer (Fermentas).

PCR

To control for a potential PCR bias, the DNA mixture was supplemented with 2 GE PhiX174 plasmid (1 GE=1.8 pg of PhiX174 corresponds to 1 microgram gDNA) that was cut with HpyCH4IV and ligated to the adaptor. PCR amplifications were conducted for up to 25 cycles. A standard aminoallyl-PCR mixture included 400 ng of the ligate, 40 microliter of 10× reaction-buffer (Sigma), 42 microliter MgCl2 [25 mM], 3 microliter aminoallyl-dNTP Mix [containing 15 mM aminoallyl-dUTP, 10 mM dTTP and 25 mM each dCTP, dGTP and dATP], 200 pmol primer (U-CG1a, AATT-1b or TA-1b, respectively), 3 microliter Taq enzyme (5 U/microliter, NEB) and water to a final volume of 400 microliter. The amplification program was as follows: an initial 5 min at 72° C. to fill in the protruding ends of the ligated DNA, 30 s denaturation at 95° C. followed by 25 cycles of 30 s at 94° C. and 2 min at 67° C., and a final extension of 5 min at 72° C. To analyze the DNA methylation patterns using small amounts of DNA template (<20 ng), we used a different protocol of amplification without aminoallyl-dUTP. Instead of Taq polymerase, PCR reactions contained 2.5 ml Phusion enzyme (2 U/microliter; Finnzyme, Oy, Finland). The amplification reaction started with an initial 5 min at 72° C., 1 min at 98° C. followed by 30 cycles of 20 s at 98° C. and 1:40 min at 68° C., and a final extension of 5 min at 72° C.

Generation of Dye-coupled Adaptor Products

Aminoallyl-PCR products were purified on Microcon Y-50 columns (millipore) according to the manufacturer's instructions, concentrated by centrifugation under vacuum, and resuspended in 9 microliter of 0.1 M sodium-bicarbonate buffer ($Na_2CO_3$/$NaHCO_3$; pH 9.0) and 2 microliter dimethyl sulfoxide (DMSO). The contents of one vial of Cy3 or Cy5 monofunctional reactive dye (Amersham Biosciences, Piscataway, N.J.) were dissolved in 72 microliter DMSO. Aminoallyl DNA (4 microgram) was mixed with 4.8 microliter of dye, briefly denatured in a heatblock at 100° C. and incubated for 2 h at 30° C. in the dark. To prevent cross reactivity between Cy5 and Cy3 samples, labeled DNA was quenched with 4.5 microliter of 4 M hydroxylamine (Sigma). Labeled tester and control samples were combined and purified in MiniElute columns (Qiagen).

The Phusion amplification products (4 microgram) were reconstituted in 29 microliter water and subjected to direct labelling. The DNA-mixture, 4 microliter of 10× reaction buffer (Fermentas), and 1 microliter random primer (Invitrogen) were denatured at 95° C. for 5 minutes, cooled on ice, and supplemented with 4 microliter 10 × dNTP mix (1 mM of each dGTP, dTTP, DATP; 0.65 mM dCTP; 0.35 mM Cy3/Cy5-dCTP; 1 mM EDTA; 10 mM Tris, pH 8.0), 2 microliter of Klenow fragments [10 U/microliter, incubated in the dark at 37° C. for 2 h and purified in MiniElute columns. The eluates were concentrated to approximately 5 microliter by vacuum centrifugation and labelling efficiency was measured by absorbance at 260 nm and 550 nm for Cy3 and 650 nm for Cy5. The frequency of dye-incorporation (FOI) was calculated with the following formulas: For Cy3: 86.52×(A550/A260) and for Cy5 incorporation: 51.92×(A650/A260). Prior to hybridization, the labeled DNA was added to the hybridization buffer (SlideHyb™ #2, Ambion, Austin, USA) containing 0.9 microgram/microliter tRNA (Sigma) and 0.1 microgram/microliter Cot-1 DNA (Roche Diagnostics), and heated to 72° C. for 5 min.

Array Hybridizations

Each microarray slide was prehybridized with a mixture consisting of DIG Easy Hyb (Roche Diagnostics), 25 microgram/ml tRNA and 200 microgram/ml BSA. The printed area was covered with the prehybridization mixture under a coverslip for 1 h at 45° C. The microarray slides were then washed in two changes of water for 2 min at 45° C., followed by two wash-steps at room temperature and a final wash-step in isopropanol for 1 min. The slides were immediately blown dry with pressurized air and stored for hybridization. The hybridization mixtures were then pipetted onto the arrays and covered with Sigma Hybri-slips. The microarrays were placed in hybridization chambers (Corning Microarray Technologies, New York, USA) and incubated on a level surface for 16 h at 37° C. in a covered water bath. The coverslips were removed by immersion of the arrays in a wash solution containing 2× SSC and 0.5% SDS (washing buffer I). The array was washed twice for 15 min at 37° C. in washing buffer I (low stringency), followed by two wash-steps in washing buffer II (0.5× SSC, 0.5% SDS), followed by 2 min of incubation in water. The slides were then rinsed quickly in isopropanol and finally dried with pressurized air.

Whole Genome Amplification

Genomic DNA was amplified using the GenomiPhi Kit (Amershamn Biosciences) according to the manufacturer's protocol. Briefly, 10 ng of GDNA (1 microliter) was mixed with 9 microliter of sample buffer, denatured at 95° C. for 3 min, cooled on ice and then added to 9 microliter of reaction buffer and 1 microliter of Phi29 DNA polymerase. The reaction was incubated at 30° C. for 16 h and then inactivated at 65° C. for 10 min.

Bisulfite sequencing

The methylation status of a number of CpG islands were analysed by direct sequencing of sodium bisulphite modified genomic DNA. Genomic DNA samples were subjected to bisulfite modification using a standard protocol, FIG. 6 shows bisulfite-modified sequence data for CpG island clones 22_B_12 (promoter region of Galectin 1) and 52_C_03 (promoter region of a brain-specific transcript, CR606704). The primer sequences for the clones shown in FIG. 6 were as follows: clone 22_B_12 was analysed using a nested approach with two sets of primers:

```
22B12F1
(GTAGAATGTTAATTTTGGGTAGAAATAAT),     SEQ ID NO: 9;

22B12R1
(CTCAACCAT CTTCTCTAAACACC),          SEQ ID NO: 10;

22B12F2
(GTTATTGAGGTTTAGAAAAGAGAAGGTAT),     SEQ ID NO: 11;

22B12R2
(ACTTATAAACCTAACTCATCATCAAACTAT),    SEQ ID NO: 12;
```

Clone 52_C_3 was analyzed with the following primers:

```
52C3F1
(AGTTTGTATTAAGGAGATTTATAAGGATAG),    SEQ ID NO: 13;

52C3R1
(AACCAACAAAACACACAAACC),             SEQ ID NO: 14;

52C3F2
(AATTTAGATTTTGAGTTTTTGAAAG),         SEQ ID NO: 15;

52C3R2
(AACACAACATAACAACAAACAAAAC),         SEQ ID NO: 16.
```

PCR was performed for the first round using one bead (approximately 10 microliter) of bisulphite modified DNA, 200 mmol dNTPs, 100 pmol each primer and 1 U of Taq polymerase (New England Biolabs) in a total. volume of 100 microliter. The cycling consisted of 3 min denaturation at 95° C. followed by 35 cycles of 30 s at 95° C.; 30 s at 56° C., 40 s at 72° C., finishing with a 5 min final extension at 72° C. The second round PCR used 2 microliter of a 1:20 dilution of the first round PCR as a template in a 20 microliter reaction. The PCR cycling consisted of 3 min denaturation at 95° C. followed by 10 cycles of a touchdown protocol of 30 s at 95° C.; 30 s at 60° C. (−1° C./cycle), 40 s at 72° C., followed by 30 cycles of 30 s at 95° C.; 30 s at 50 deg C., 40 s at 72° C., finishing with 5 min of final extension at 72° C. PCR products were purified with the MinElute purification kit (Qiagen) and cloned directly into the pGEM-T vector (Promega). Fifteen clones from each PCR were sequenced directly with the M13 reverse primer using ABI Prism Big Dye Terminator Cycle Sequencing Ready reaction kit (PE Applied Biosystem), and analysed on an ABI Avante 3100.

Genomic DNA

Genomice DNA from all tissues was purified with standard laboratory methods (Phenol/Chloroform or Qiagen Blood and Cell DNA Midi columns). To avoid cross reactivity of amine groups with the aminoallyl-labeling procedure, DNA samples were stored in 0.5 M POPSO buffer (pH 8.0) instead of Tris-EDTA. Male placental DNA was purchased from Sigma and the post-mortem brain samples were provided by the Stanley Medical Research Institute.

Example 1 shows that the array based technology for DNA modification analysis enables a highly parallel screening of numerous restriction fragments that represent DNA methylation profiles over large segments of genomic DNA.

Compared to the existing approaches to assist in the detection of DNA modification, the present methods exhibit several advantages. The earlier approach used a fractionation in a sucrose gradient, which requires large amount of DNA template and is rather imprecise in terms of the upper limit of the fragments that are subjected to hybridization. The other microarray-based methods for DNA methylation analysis can be categorized into two main classes: i) approaches that identify bisulfite induced C to T transitions, and ii) approaches that are based on the enrichment of the hypermethylation fraction of genomic DNA. In the bisulfite arrays, each tested CpG is represented by a pair of either C(G) or T(A), containing oligonucleotides that measure the C(G)/T(A) ratio in the bisulfite treated DNA (corresponding to metC/C in the native DNA). Although informative and precise, the microarray can contain only a limited number of oligonucleotides because treatment with bisulfite degenerates the four-nucleotide code, which results in the loss of specificity of a large portion of the genome. For example, after bisulfite treatment all of the possible 16 permutations of a four base sequences containing unmethylated C and T (CCCC, CTCT, CCCT, CCTT, TCTC, TTTC, TTTT, etc . . . ) will become identical TTTT. Furthermore, it is difficult to design suitable oligonucleotides that would exhibit similar melting temperatures since the specificity of base discrimination varies considerably. Using the methods of the present invention, the arrays can contain practically an unlimited number of oligonucleotides: from individual genes to entire chromosomes represented by millions of oligonucleotides on glass chips. Whole genome tiling arrays are already available for *Arabidopsis thaliana* and *E.coli*, and will soon be available for the entire human genome.

Another advantage of the methylation profiling methods of the present invention is the possibility to work with limited DNA resources. Although the standard protocol requires from 0.5 mg-1 mg of genomic DNA, the amount of the template DNA can be significantly lower. Methylation patterns at the catecol-o-methyl transferase (COMT) region generated from a relatively small number of Jurkat tissue culture cells (up to 500 cells, or 3 ng) did not reveal any significant differences compared to the methylation patterns generated from a substantially larger number of cells from the same tissue (data not shown). It seems feasible to apply the enrichment protocol also for single cells, which would allow a quantitative measurement of methylation.

Example 2

Profiling of epiG DRD2 Using Microarrays

In an embodiment of the present invention, the method may be employed to profile epiG DRD2 using microarrays. In the embodiment, a microarray is designed that is specific for epiG profiling of the full length of DRD2, including the very long (~250 kb) intron 1. Without wishing to be limiting in any manner, the general principle of the 'epiG' array comprises the hybridization of the hypomethylated (or hypermethylated) fraction of genomic DNA (or the DNA fraction associated with acetylated, methylated, for example, but not limited to histones) to the microarray containing oligonucleotides that represent the genomic region of interest. Intensity of hybridization correlates with the DNA methylation status at the genomic locus homologous to a specific oligonucleotide on the array. The microarray-based epiG analysis of DRD2 comprises the following steps:

i) Oligonucleotides for microarrays. Using the publicly available human genome sequence of DRD2 plus wide upstream and downstream regions, 40-50 base oligonucleotides (with amino modifiers at the 5' end) that cover the testable genomic region of .about.350 kb are designed. See genomeDOTucscDOTedu, wherein "DOT" is ".". In epiG studies, sufficient coverage is achieved by about 3-5 (or more) oligonucleotides per kilobase of genomic DNA. Repetitive DNA elements maybe excluded using the RepeatMasker, which reduces the length of the target sequence from about 350 kb to about 200 kb. This requires about 800 oligonucleotides that will be synthesized for example, but not limited to at Qiagen, and then spotted on the glass at a specific location, for example, but not limited to the UHN Microarray Facility.

ii) DNA samples are extracted from the D2 expressing cell lines treated with i) haloperidol; ii) clozapine; iii) haloperidol+VPA; iv) clozapine+VPA; v) VPA only, and the control DNA is extracted from the identical cell line of the same age, but without exposure to an antipsychotic. Two D2 receptor expressing cell lines are used: HTB-18 (Y-79)57 (available from ATCC), and hNT58 (available from Layton BioScience, Inc.).

iii) Time intervals. DNA samples are extracted from each of the above treatments after 1, 6, and 24 hours, and then 3, and 7 days (time intervals selected arbitrarily).

iv) Preparation of the hypomethylated fraction of genomic DNA. Without wishing to be bound by theory, a cocktail of methylation sensitive restriction enzymes, such as HpaII, Hin6I, AciI, TaiI, and a recent addition of McrBC, may interrogate 25%-50% of all CpGs (Schumacher, Petronis et al; in preparation). In order to enrich the hypomethylated fraction of genomic DNA, after digestion with DNA methylation sensitive restriction enzymes, DNA adaptors are ligated to the restriction fragments, which is followed by subsequent polymerase chain reaction (PCR) amplification using primers that are complementary to the adaptors. PCR conditions are adjusted in such a way that only fragments that are less than 1 kb (i.e. short, digested, and therefore unmethylated) will amplify preferentially. The hypomethylated fraction of genomic DNA from matching pairs are then labeled with Cy3- (e.g., DNA from cells treated with haloperidol) and Cy5- (e.g., DNA from the control cells) and co-hybridized to the microarray. Each comparison is performed in duplicate or greater, and averaged intensities are used for the further analyses.

v) Hybridizations are performed using standard array protocols as described herein, and scanning of microarrays may be perfromed at the UHN Microarray Facility using the GenePix software (Pro 3.1). The software gives a raw data output, which is normalized by Normalzing Suite 2.0 and subjected to further analysis using the home-made Excel Macros. A set of experiments on a gene using a microarray of 100+ oligos (more recently with 300+ oligos), shows consistent results of DNA methylation profiles of this region.

vi) Data analysis. The analysis of hybridization profiles and identification of the drug induced epiG changes is straightforward. The hypomethylated fraction of DNA from treated cell lines is compared to the one from an untreated control, and scatter plot diagrams for each comparison will be generated. Hybridization signals that deviate from the regression line are sought.

The method of enriching hyper- and hypomethylated DNA fractions is different and improved compared to previously published methods. The method as disclosed herein is the first that uses a novel strategy for the enrichment of hypomethylated and hypermethylated fraction of genomic DNA, that efficiently compares the methylation status of CpG dinucleotides in test and control samples across large and very large segments of genomic DNA. In addition, the method employs an informative combination of methylation sensitive restriction enzymes that cleave or do not cleave DNA containing methyl-cytosine on one or both stands and permits for a more stringent and detailed analysis of methylation profiles compared to the other methods known in the art.

The present invention also allows the analysis of very small tissue samples (e.g. from laser micro-dissected samples). The necessary amount of genomic DNA (gDNA) for one analysis maybe as low as 50 pg (<10 cells).

The array-based method as described above has also several advantages compared to the bisulfite-dependent methods. The methods that rely on the bisulfite method are commonly used but require labor-intensive and time-consuming cloning and sequencing steps, which can be skipped when using the method of the present invention. Further, the bisulfite-based strategies provide only information about specific residues that have been chosen in advance as being informative, whereas the method as described herein may be used to screen complete genomes for methylation differences. Moreover, if the bisulfite approach is used in the microarray format, the technique requires numerous permutations of oligonucleotides, which dramatically increases the costs for oligonucleotides or is limited to a relatively short DNA segment.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A method of analyzing the methylation state of one or more nucleotide sequences comprising the steps of:
   a) selecting one or more genomic test nucleotide sequences from one or more subjects that exhibit a phenotype of interest, and one or more corresponding genomic control sequences from one or more control subjects that lack the phenotype of interest;
   b) digesting the genomic test nucleotide sequences and separately digesting genomic control sequences with one or more methylation-sensitive restriction endonucleases that cut unmethylated sequences but not methylated sequences, to produce ends that can be ligated to an adaptor nucleotide sequence;
   c) ligating adaptor nucleotide sequences to the ends produced from step b) to produce ligated sequences;
   d) cleaving the ligated sequences with one or more methylation-specific endonucleases that cut methylated sequences but not unmethylated sequences, to produce amplifiable test nucleotide sequences, non-amplifiable nucleotide sequences, amplifiable control nucleotides sequences and non-amplifiable control nucleotide sequences;
   e) amplifying the amplifiable test nucleotide sequences and amplifiable control nucleotide sequences to produce amplified test nucleotide sequences and amplified control nucleotide sequences;
   f) labeling the amplified test nucleotide sequences from step e) with a first label, and labeling the amplified control nucleotide sequence from step e) with a second label;
   g) hybridizing the labeled products of step f) with an array comprising a series of nucleotide sequences that are capable of hybridizing thereto; and
   h) determining the ratio of the signals emitted by the first label relative to the second label for each hybridized nucleotide sequence on the array.

2. The method of claim 1, further comprising a step of correcting for the effect of DNA sequence variation:
   i) amplifying the genomic test nucleotide sequences and separately amplifying the genomic control sequences with a DNA polymerase to produce an unmethylated copy of the genomic test nucleotide sequences and an unmethylated copy of the genomic control sequences;
   ii) treating the unmethylated copy of the genomic test nucleotide sequences and separately treating the unmethylated copy of the genomic control sequences with restriction endonuclease digestion, adaptor ligation, amplification, labeling, array hybridization, and ratio determination steps that are equivalent to corresponding steps b), c) and e-h); and
   iii) comparing the one or more ratios determined in step ii) to the one or more ratios determined in step h).

3. The method of claim 1, wherein the methylation specific endonuclease is McrBC.

4. The method of claim 1, wherein the methylation-sensitive restriction endonuclease comprises HpaII, Bsul51 (ClaI), Hin61, AciI (SsiI), TaiI, or any combination thereof.

5. The method of claim 1, wherein step f) further comprises labeling the non-amplified test nucleotide sequences from step d) with the first label, and labeling the non-amplified control nucleotide sequences from step d) with a second label.

6. The method of claim 1, wherein the phenotype of interest comprises cancer, diabetes, Alzheimer's disease, or schizophrenia, multiple sclerosis, psoriasis, atherosclerosis, asthma, autism, or rheumatoid arthritis.

7. The method of claim 1, wherein the first label, second label or both are chemically reactive fluorophores.

8. The method of claim 1, wherein said chemically reactive fluorophores are independently Cy 3 or Cy 5.

9. A method of identifying DNA sequence variation in a methylation-state-analysis of one or more nucleotide sequences comprising the steps of:
   a) selecting one or more genomic test nucleotide sequence from one or more subjects that exhibit a disease phenotype of interest and one or more corresponding genomic control sequences from one or more control subjects that lack the disease phenotype of interest;
   b) amplifying the genomic test nucleotide sequences and separately amplifying the genomic control sequences with a DNA polymerase, to produce an unmethylated copy of the genomic test nucleotide sequences and an unmethylated copy of the genomic control sequences;
   c) treating the unmethylated copy of the genomic test nucleotide sequences and separately treating the unmethylated copy of the genomic control sequences with restriction endonuclease digestion, adaptor ligation, amplification, labeling, array hybridization, and ratio determination steps, and;
   d) comparing the one or more ratios determined in step c) to the one or more ratios of the methylation-state-analysis, thereby identifying DNA sequence variation in the methylation-state-analysis.

* * * * *

SEQUENCE LISTING

<160> NUMBER OF SEQ ID NOS: 16

<210> SEQ ID NO 1
<211> LENGTH: 21
<212> TYPE: DNA
<213> ORGANISM: Artificial Sequence
<220> FEATURE:
<223> OTHER INFORMATION: human sequence CpG-overhang adaptor

```
<400> SEQUENCE: 1
cgtggagact gactaccaga t                                            21

<210> SEQ ID NO 2
<211> LENGTH: 25
<212> TYPE: DNA
<213> ORGANISM: Artificial Sequence
<220> FEATURE:
<223> OTHER INFORMATION: human sequence CpG-overhang adaptor

<400> SEQUENCE: 2
agttacatct ggtagtcagt ctcca                                        25

<210> SEQ ID NO 3
<211> LENGTH: 17
<212> TYPE: DNA
<213> ORGANISM: Artificial Sequence
<220> FEATURE:
<223> OTHER INFORMATION: human sequence ACGT-overhang adaptor

<400> SEQUENCE: 3
gagactgact accagat                                                 17

<210> SEQ ID NO 4
<211> LENGTH: 27
<212> TYPE: DNA
<213> ORGANISM: Artificial Sequence
<220> FEATURE:
<223> OTHER INFORMATION: human sequence ACGT-overhang adaptor

<400> SEQUENCE: 4
agttacatct ggtagtcagt ctcacgt                                      27

<210> SEQ ID NO 5
<211> LENGTH: 17
<212> TYPE: DNA
<213> ORGANISM: Artificial Sequence
<220> FEATURE:
<223> OTHER INFORMATION: human sequence AATT-overhang adaptor

<400> SEQUENCE: 5
gagactgact accagat                                                 17

<210> SEQ ID NO 6
<211> LENGTH: 27
<212> TYPE: DNA
<213> ORGANISM: Artificial Sequence
<220> FEATURE:
<223> OTHER INFORMATION: human sequence AATT-overhang adaptor

<400> SEQUENCE: 6
agttacatct ggtagtcagt ctcaatt                                      27

<210> SEQ ID NO 7
<211> LENGTH: 20
<212> TYPE: DNA
<213> ORGANISM: Artificial Sequence
<220> FEATURE:
<223> OTHER INFORMATION: human sequence TA-overhang adaptor

<400> SEQUENCE: 7
tatgagactg actaccagat                                              20

<210> SEQ ID NO 8
<211> LENGTH: 24
<212> TYPE: DNA
```

```
<213> ORGANISM: Artificial Sequence
<220> FEATURE:
<223> OTHER INFORMATION: human sequence AATT-overhang adaptor

<400> SEQUENCE: 8
agttacatct ggtagtcagt ctca                                         24

<210> SEQ ID NO 9
<211> LENGTH: 29
<212> TYPE: DNA
<213> ORGANISM: Artificial Sequence
<220> FEATURE:
<223> OTHER INFORMATION: human sequence CpG island methylation primer

<400> SEQUENCE: 9
gtagaatgtt aattttgggt agaaataat                                    29

<210> SEQ ID NO 10
<211> LENGTH: 23
<212> TYPE: DNA
<213> ORGANISM: Artificial Sequence
<220> FEATURE:
<223> OTHER INFORMATION: human sequence CpG island methylation primer

<400> SEQUENCE: 10
ctcaaccatc ttctctaaac acc                                          23

<210> SEQ ID NO 11
<211> LENGTH: 29
<212> TYPE: DNA
<213> ORGANISM: Artificial Sequence
<220> FEATURE:
<223> OTHER INFORMATION: human sequence CpG island methylation primer

<400> SEQUENCE: 11
gttattgagg tttagaaaag agaaggtat                                    29

<210> SEQ ID NO 12
<211> LENGTH: 30
<212> TYPE: DNA
<213> ORGANISM: Artificial Sequence
<220> FEATURE:
<223> OTHER INFORMATION: human sequence CpG island methylation primer

<400> SEQUENCE: 12
acttataaac ctaactcatc atcaaactat                                   30

<210> SEQ ID NO 13
<211> LENGTH: 30
<212> TYPE: DNA
<213> ORGANISM: Artificial Sequence
<220> FEATURE:
<223> OTHER INFORMATION: human sequence CpG island methylation primer

<400> SEQUENCE: 13
agtttgtatt aaggagattt ataaggatag                                   30

<210> SEQ ID NO 14
<211> LENGTH: 21
<212> TYPE: DNA
<213> ORGANISM: Artificial Sequence
<220> FEATURE:
<223> OTHER INFORMATION: human sequence CpG island methylation primer

<400> SEQUENCE: 14
aaccaacaaa acacacaaac c                                            21
```

```
<210> SEQ ID NO 15
<211> LENGTH: 25
<212> TYPE: DNA
<213> ORGANISM: Artificial Sequence
<220> FEATURE:
<223> OTHER INFORMATION: human sequence CpG island methylation primer

<400> SEQUENCE: 15
aatttagatt ttgagttttt gaaag                                      25

<210> SEQ ID NO 16
<211> LENGTH: 25
<212> TYPE: DNA
<213> ORGANISM: Artificial Sequence
<220> FEATURE:
<223> OTHER INFORMATION: human sequence CpG island methylation primer

<400> SEQUENCE: 16
aacacaacat aacaacaaac aaaac                                      25
```